United States Patent
Morello et al.

(10) Patent No.: US 12,040,685 B2
(45) Date of Patent: Jul. 16, 2024

(54) ELECTRIC MOTOR WITH PASSIVE AND ACTIVE MAGNETIC BEARINGS

(71) Applicant: Veritium Research LLC, Fort Lee, NJ (US)

(72) Inventors: Gino Morello, Fort Lee, NJ (US); Steven Prina, Fort Lee, NJ (US)

(73) Assignee: VERITIUM RESEARCH LLC, Fort Lee, NJ (US)

( * ) Notice: Subject to any disclaimer, the term of this patent is extended or adjusted under 35 U.S.C. 154(b) by 0 days.

(21) Appl. No.: 17/921,029

(22) PCT Filed: Apr. 23, 2021

(86) PCT No.: PCT/US2021/028781
§ 371 (c)(1),
(2) Date: Oct. 24, 2022

(87) PCT Pub. No.: WO2021/216960
PCT Pub. Date: Oct. 28, 2021

(65) Prior Publication Data
US 2023/0121406 A1    Apr. 20, 2023

Related U.S. Application Data

(60) Provisional application No. 63/015,074, filed on Apr. 24, 2020.

(51) Int. Cl.
*H02K 7/09* (2006.01)
*F16C 32/04* (2006.01)
(Continued)

(52) U.S. Cl.
CPC .......... *H02K 7/09* (2013.01); *F16C 32/0408* (2013.01); *F16C 32/0421* (2013.01);
(Continued)

(58) Field of Classification Search
CPC  A61M 60/822; A61M 60/117; A61M 60/178; A61M 60/226; A61M 60/38;
(Continued)

(56) References Cited

U.S. PATENT DOCUMENTS

2003/0128026 A1    7/2003   Lutz
2012/0274167 A1   11/2012   Kim et al.
(Continued)

FOREIGN PATENT DOCUMENTS

WO    01/084693 A1    11/2001

OTHER PUBLICATIONS

International Search Report and Written Opinion of the International Searching Authority for International Patent Application No. PCT/US2021/028781 mailed Jul. 28, 2021, 8 pages.

*Primary Examiner* — Alexander A Singh
(74) *Attorney, Agent, or Firm* — MERCHANT & GOULD P.C.

(57) ABSTRACT

A magnetically levitated motor includes a stator, a rotor configured to rotate relative to the stator, and a passive radial magnetic bearing configured to support the rotor relative to the stator in a radial direction. An active longitudinal magnetic bearing is configured to selectively position the rotor relative to the stator in an axial direction.

20 Claims, 15 Drawing Sheets

(51) Int. Cl.
  *H02K 11/215*   (2016.01)
  *A61M 60/117*   (2021.01)
  *A61M 60/178*   (2021.01)
  *A61M 60/226*   (2021.01)
  *A61M 60/419*   (2021.01)
  *A61M 60/822*   (2021.01)

(52) U.S. Cl.
  CPC ........ *F16C 32/044* (2013.01); *F16C 32/0478* (2013.01); *H02K 11/215* (2016.01); *A61M 60/117* (2021.01); *A61M 60/178* (2021.01); *A61M 60/226* (2021.01); *A61M 60/419* (2021.01); *A61M 60/822* (2021.01); *F16C 2316/18* (2013.01)

(58) Field of Classification Search
  CPC ............... A61M 60/419; A61M 60/538; F16C 32/0478; F16C 2316/18; F16C 32/0446; F16C 32/0495; F16C 2380/26; F16C 32/0425; F16C 32/0408; F16C 32/0406; F16C 32/0419; F16C 32/0421; F16C 32/044; H02K 7/09; H02K 11/215; H02K 7/14; H02K 1/02; H02K 2213/03; Y02B 10/30; Y02E 10/72
  USPC ....................................................... 310/90.5
  See application file for complete search history.

(56)              References Cited

U.S. PATENT DOCUMENTS

2013/0316624 A1     11/2013  Diehl et al.
2023/0121406 A1 *   4/2023   Morello .............. A61M 60/419
                                                            600/16

* cited by examiner

ELECTRIC MOTOR WITH PASSIVE AND ACTIVE MAGNETIC BEARINGS

CROSS-REFERENCE TO RELATED APPLICATION

This application is being filed on Apr. 23, 2021, as a PCT International Patent Application and claims priority to U.S. Provisional Patent Application No. 63/015,074, filed Apr. 24, 2020, the disclosure of which is hereby incorporated by reference in its entirety.

GOVERNMENT LICENSE RIGHTS

This application is a National Stage Application of PCT/US2021/028781, filed Apr. 23, 2021, which claims priority to U.S. Provisional Patent Application No. 63/015,074, filed Apr. 24, 2020, the disclosures of which are hereby incorporated by reference in their entireties. To the extent appropriate, a claim of priority is made to the above referenced application.

BACKGROUND

This disclosure relates generally to a magnetically levitated motor. The use of magnetic levitation of a rotor in a motor allows a lack of contact and thus no or reduced wear and friction. This increases efficiency, reduces maintenance costs, and increases the useful life of the system. Magnetic levitation is a method by which an object is suspended in the air with no support other than magnetic fields. The magnetic fields are used to counteract the gravitational pull and any other counter accelerations.

SUMMARY

In accordance with disclosed embodiments, a magnetically levitated motor includes a stator, a rotor configured to rotate relative to the stator, and a radial magnetic bearing configured to support the rotor relative to the stator in a radial direction. An active longitudinal magnetic bearing is configured to selectively position the rotor relative to the stator in an axial direction.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion. In addition, the drawings are illustrative as examples of embodiments of the invention and are not intended to be limiting.

DETAILED DESCRIPTION

Figure 1:
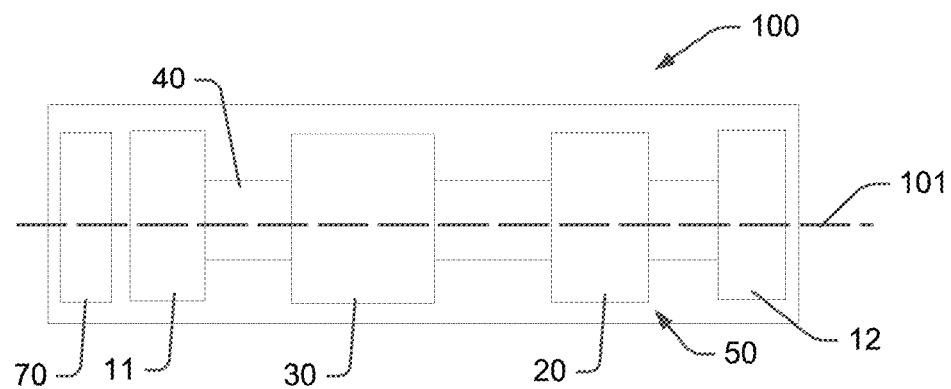
FIG. 1 is a block diagram illustrating aspects of a magnetically levitated motor in accordance with disclosed examples.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Aspects of the present disclosure relate generally to a magnetically levitated motor. During steady-state operation, the rotor assembly is magnetically levitated to preclude the use of mechanical bearings (e.g. jewels, pins, cones, balls, etc.) and minimize wear.

A variety of applications employ magnetic levitation, including (but not limited to)
- Biomedical engineering including Blood Pumps, Stirring Systems, Agitation Systems, Extracorporeal mechanical oxygenators (ECMO), Cardio Pulmonary Bypass (CPB), mechanical circulatory assist (MCS)
- Transportation engineering (magnetically levitated trains, flying cars, or personal rapid transit (PRT), etc.),
- Environmental engineering (small and huge wind turbines: at home, office, industry, etc.),
- Aerospace engineering (spacecraft, rocket, etc.),
- Military weapons engineering (rocket, gun, etc.),
- Nuclear engineering (the centrifuge of nuclear reactor),
- Civil engineering including building facilities and air conditioning systems (magnetic bearing, elevator, lift, fan, compressor, chiller, pump, gas pump, geothermal heat pumps, etc.),
- Chemical engineering (analyzing foods and beverages, etc.),
- Electrical engineering (magnet, etc.),
- Architectural engineering and interior design engineering including household and administrative appliances (lamp, chair, sofa, bed, washing machine, room, toys (train, levitating spacemen over the spaceship, etc.), stationery (pen), etc.),
- Automotive engineering (car, etc.),
- Advertising engineering (levitating everything considered inside, or above various frames can be selected).

Some disclosed examples provide a blood pump employing a magnetically levitated motor. Generally, blood pump systems are employed in either of two circumstances. First a blood pump may completely replace a human heart that is not functioning properly, or second, a blood pump may boost blood circulation in patients whose heart is still functioning although pumping at an inadequate rate. The blood pump may be external, partially implanted or completely implanted. For example, a ventricle assist device (VAD) is a miniaturized pump designed to provide additional blood flow to patients who suffer from heart disease. The device is attached between the apex of the left ventricle and the aorta.

Limitations of existing blood pump technology may include inability to reduce pump size (small body habitus of the neonate and infant populations), anatomical fit (thoracic orientation), cannula configuration (underlying vascular anatomy associated with congenital cardiac anomalies), post-operative management, and cost effectiveness (materials, multiple systems, and complexity). "Pediatric Mismatch" can occur when pediatric surgeons implant inadequate adult devices that are not designed to support pediatric patients. In such situations, complications such as thrombus formation and stroke may occur at higher than acceptable rates. Some known blood pump practice relies on using multiple devices with differing modes of operation in a variety of settings that are operated by users with varying skill sets, which may contribute to the risk of human errors. Still further, existing blood pump systems are often cost prohibitive. In 2012, the direct and indirect costs of heart failure (HF) treatment in the US was $31 billion and is projected to increase to $70 billion by 2030, demonstrating the need for simple, low-cost MCS technology.

Some motors disclosed herein include magnetic bearings configured to support the rotating portion (i.e. rotor) of the motor, offsetting hydraulic and inertial forces. The bearing forces are generated by separate passive magnetic bearings positioned on the sides of the motor block within the motor. The motor generates the torque and the longitudinal magnetic bearing force needed to suspend the rotor. By managing the height of the rotor relative to its diameter, it is possible to stabilize three spatial degrees of freedom passively. In some embodiments, one active longitudinal magnetic bearing is used for axial (i.e. longitudinal) positioning of the rotor. A compact microcontroller-based control system with a servo amplifier enables precise regulation of the rotor speed and position.

External magnetic position sensors are used to provide feedback for the rotor's longitudinal position to the control system to actively control the rotor longitudinal position. The system's microcontroller and related electronics are used to regulate the magnetic fields so that the rotor is positioned optimally between the passive magnetic bearings. The electronics also precisely regulate rotational speed of the rotor. The tilting of the rotor is passively stabilized. In the exemplary embodiment of a blood pump, the rotor assembly is floated and prevented from contact within the pump housing and levitated by magnetic fields transmitted through the motor well and pump walls.

FIG. 1 conceptually illustrates various aspects of a magnetically levitated motor 100 in accordance with example embodiments. The illustrated motor 100 includes first and second magnetic radial bearings 10, 12, an axial or longitudinal bearing 20, and a motor actuator 30. A rotor 40 is configured to rotate relative to a stator assembly 50 in response to a rotating force generated by the motor actuator 30. The passive radial magnetic bearings 10, 12 are positioned at opposite ends of the rotor assembly 40 and configured to passively position the rotor 40 radially within the stator assembly 50, for example, such that the rotor 40 and stator 50 are coaxial during operation of the motor 100. The longitudinal magnetic bearing 20 is configured to actively position the rotor assembly 40 in the axial or longitudinal direction (i.e. along the motor axis 101. For example, in some implementations (such as a blood pump) the motor 100 may be employed in a vertical orientation, i.e. the motor axis 101 extends vertically. When the motor 100 is in an off state (i.e. rotor 40 is not rotating), the rotor 40 settles down against the motor or pump case (for a pump implementation) due to gravity or due to axial forces produced by the PMBs. The active longitudinal magnetic bearing 20 is used to levitate the rotor 40 in a safe, stable, and efficient manner. A motor controller 70 is provided for sensing and controlling various parameters of the rotor 40 as will be discussed further below.

The VCA 120 produces an axial force to overcome unstable axial forces of the first and second PMBs 110, 112 and position the rotor assembly 140 axially during motor startup as well as during normal expected operation. Once enabled, the VCA 120 and a position feedback system of the controller 70 maintain the rotor assembly 140 centered within the PMBs 110, 112.

In some embodiments, the radial bearings 10, 12 may be actuated so as to provide the desired rotational force for rotating the rotor 40 relative to the stator 50. In such implementations, the motor actuator 30 may be eliminated.

Figure 2:
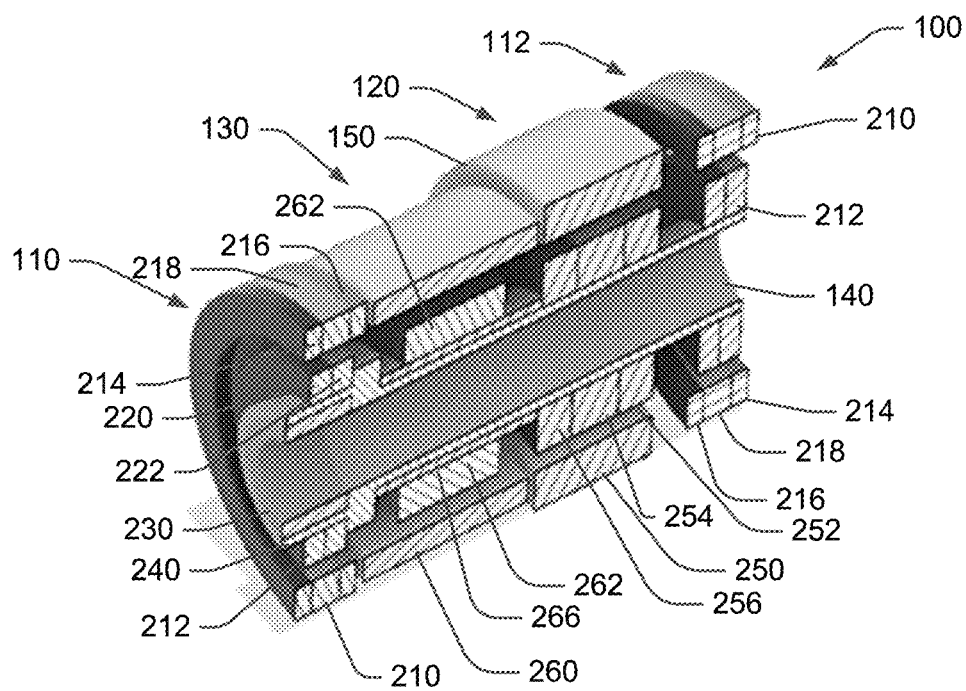
FIG. 2 is a perspective section view illustrating further aspects of an embodiment of a magnetically levitated motor.

FIG. 2 is a perspective cross section view illustrating further aspects of the magnetically levitated motor 100 in accordance with disclosed embodiments. The stator 50 includes a stator assembly 150 and the rotor 40 includes a rotor assembly 140 configured to rotate relative to the stator assembly. In the example of FIG. 2, the radial bearings 10, 12 employ a passive magnet bearing (PMB) system 110, 112 that makes use of Halbach topologies to create radial magnetic bearings. First and second PMBs 110, 112 are positioned at opposite ends of the rotor assembly 140. Finite element simulations of the assembly identified the stabilizing forces required. One drawback to the passive magnetic bearing is the relatively high unstable axial forces generated if the inner and outer bearing components are not aligned axially. Therefore, the design was optimized to minimize the ratio of axial to radial force production. The unstable axial forces are compensated by the PMBs 110, 112.

Figure 3:
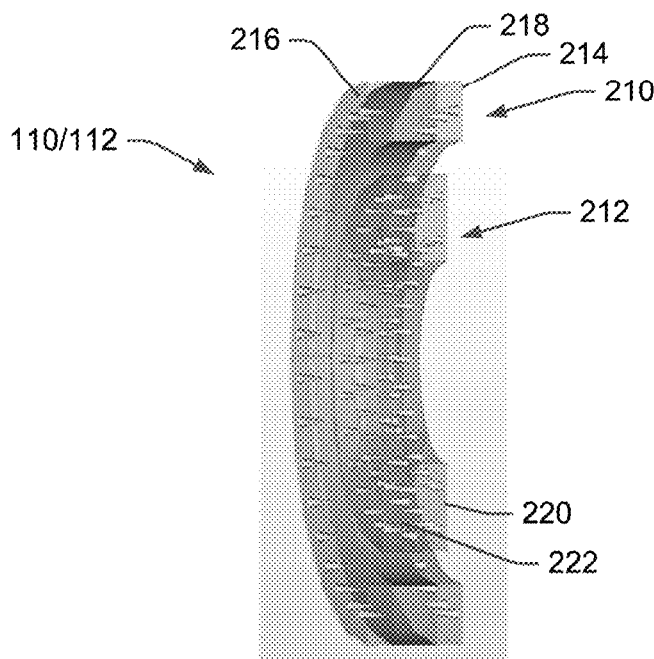
FIG. 3 is a cross section view illustrating aspects of an example of a passive magnetic bearing (PMB) stator and PMB rotor of the magnetically levitated motor shown in FIG. 2.

The first and second PMBs 110, 112 each include a PMB stator 210 and a PMB rotor 212. FIG. 3 is a cross section view illustrating aspects of the PMB stator 210 and PMB rotor 212. Each of the PMB stators 210 includes two outer components on either side of an inner component. The outer components are cylindrically shaped axially oriented permanent magnets 214, 216 that are arranged in a bucking configuration (i.e. the "North" sides face one another). The center component is a spacer 218 made from a non-magnetic material in some embodiments. As used herein, a non-magnetic material may include a hard or soft magnetic material. A hard magnetic material is a permanent magnet that retains a high amount of residual magnetism after the magnetizing field is removed. A soft magnetic material is easily magnetized and demagnetized. For instance, steel and retains a low level of residual magnetism. Plastic is a further example of a non-magnetic material. Further examples include austenitic stainless steel, such as the 300 series, which are also non-magnetic. In still further embodiments, the spacer 218 could be a permanent magnet magnetized radially. The PMBs 110, 112 function by virtue of the radial magnetic field that is created. The PMB rotors 212 each include two cylindrically shaped axially oriented permanent magnets 220, 222 that are arranged in a bucking configuration (i.e. the "North" sides face one another).

Figure 4:
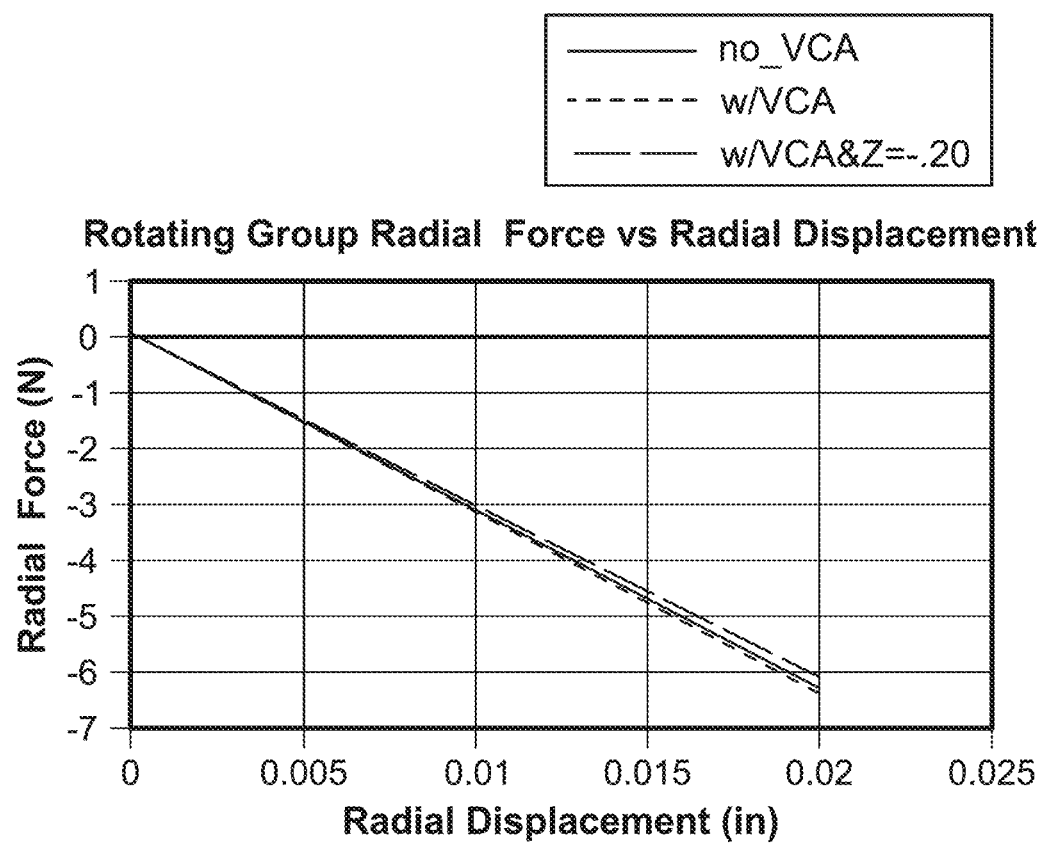
FIG. 4 is a chart showing Radial Restoring Forces vs Radial Displacement from a magnetic analysis of the levitated motor shown in FIG. 2.

In certain embodiments, optimization of the PMB was achieved by varying both radial and axial thicknesses of the components and comparing resulting stable radial forces and unstable axial forces. The goal was to achieve sufficient radial stiffness while minimizing the unstable axial forces. The bearing stiffness was assessed by simulating the forces as the rotor assembly 140 is displaced radially from its centered position. FIG. 4 shows Radial Restoring Forces vs Radial Displacement from a magnetic analysis resulting from three conditions: 1) when the rotor assembly 140 is also centered axially and the VCA and motor are off; 2) centered axially and VCA and motor are on; 3) the rotor assembly 140 is offset axially by 0.020 inch and the VCA and motor are on. At the midpoint of the radial gap (0.010 inch) the PMB system produces approximately 3.1N of radial restoring force. There is very little influence due to the VCA under these conditions.

Figure 5:
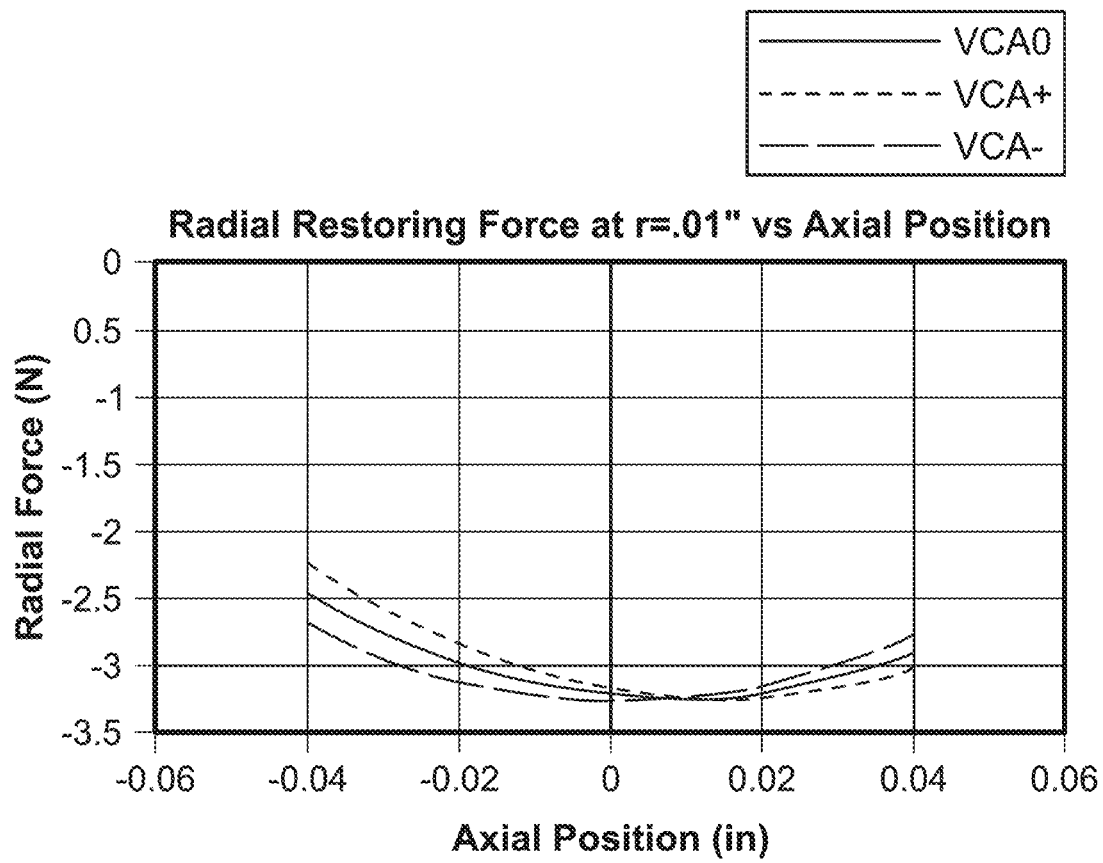
FIG. 5 is a chart showing Radial Restoring Forces vs Axial Displacement from a magnetic analysis the levitated motor shown in FIG. 2.

To further assess the impact on axial position variation the rotor assembly 140 was shifted radially from its radially centered position by 0.010 inch, which is the midpoint of the physical radial gap. Then the rotor assembly 140 was shifted axially from its centered position by 0.040 inch and the simulation was run as the axial position was varied from −0.04 inch to +0.04 inch. This process was repeated for three cases: one with the VCA unenergized and two others with the VCA energized with positive and then negative current. The results are shown in FIG. 5. The VCA operation does impact the radial restoring force but not significantly over the estimated operating range of +/−0.020 inch. The total radial restoring force varies from −2.85N to −0.315N over this range.

Figure 6:
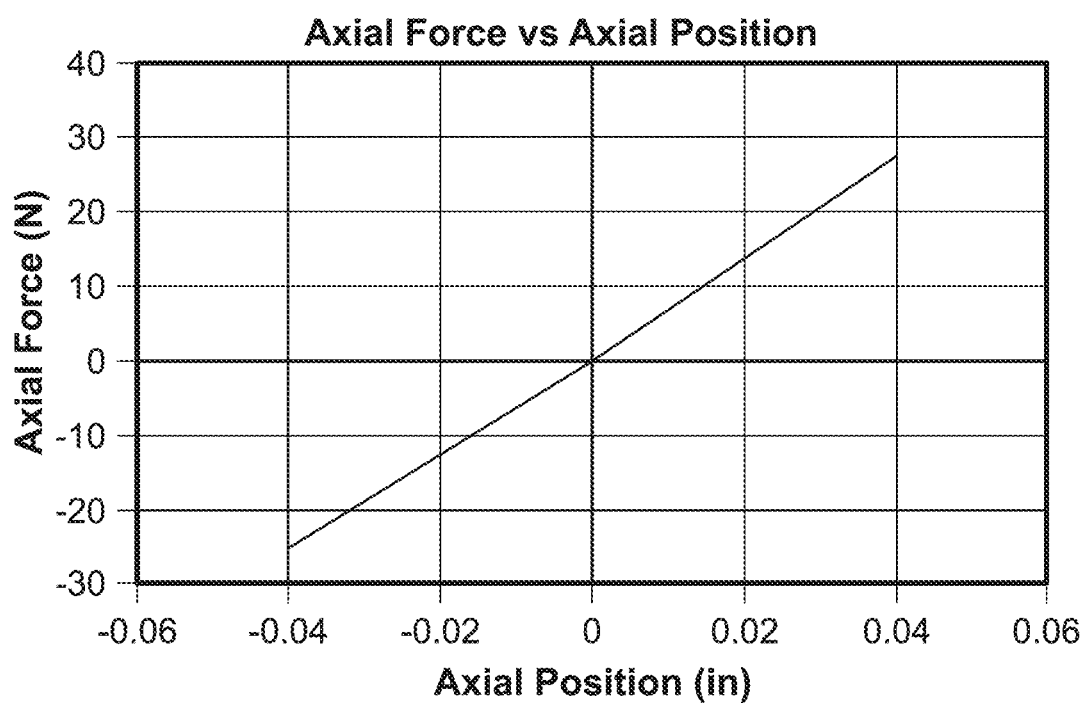
FIG. 6 is a chart showing Axial Force vs Axial Position from a magnetic analysis of the levitated motor shown in FIG. 2.

As noted previously the PMBs produce an unstable axial force. The unstable axial forces can be large and many multiples of the stabilizing radial forces. The proposed design minimized the ratio of peak unstable axial force to peak radial restoring force within the planned operating displacements. FIG. 6 shows the unstable axial force over an axial displacement of +/−0.04 inch from centered. The VCA was not energized in this simulation. Given the desired operating range of +/−0.020 inch the VCA will need to produce up to +/−14N to maintain the position of the rotor assembly 140.

Figure 7:
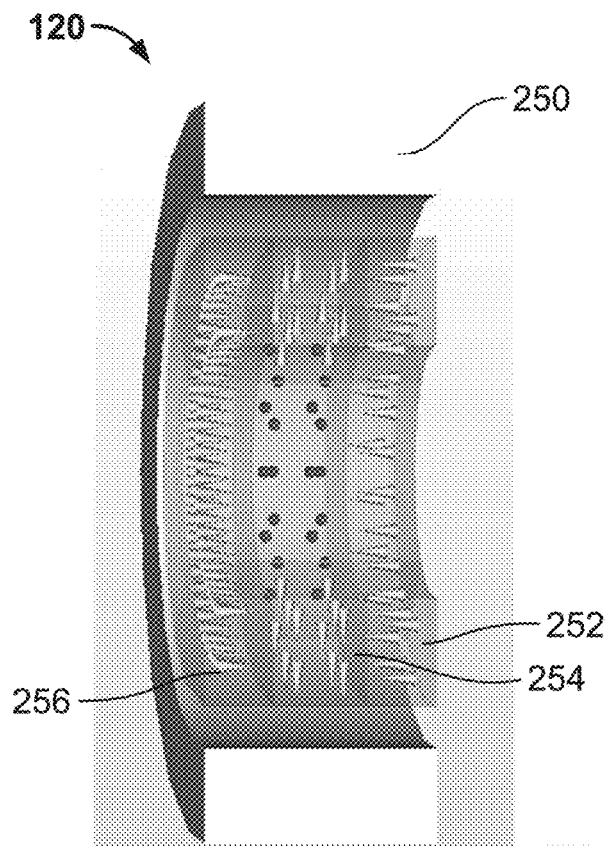
FIG. 7 is a cross section view illustrating the voice coil actuator (VCA) rotor magnetic polarities and stator of the magnetically levitated motor shown in FIG. 2.

The active axial bearing 20 employs, for example, a solenoidal voice coil magnetic actuator (VCA) 120 configured to control the axial position of a floating, rotatable rotor assembly 140. The VCA includes VCA rotor magnets 252, 254, 256 attached to a rotor tube 240 of the rotor assembly 140, and a VCA winding 250 that extends around the VCA rotor magnets 252, 254, 256. FIG. 7 is a cross section view illustrating the VCA rotor and stator, and the VCA rotor magnet orientation.

Some examples of the VCA rotor also use Halbach magnet topology. The two outer VCA magnets 252, 256 are cylindrically shaped axially oriented magnets that are arranged in a bucking configuration (i.e. the "North" sides face one another). The center VCA magnet 254 is a set of 90-degree segments that are magnetized straight through in a direction that points from the inner radius to the outer radius. This arrangement approximates a cylindrical magnet that is radially oriented.

The VCA 120 is part of a position feedback system that senses the axial position of the floating rotor assembly 140 via magnetic position sensors. In the illustrated example, the magnetic position sensors include a position sensing permanent magnet 230 mounted at the base of the rotor assembly 140 adjacent the magnets 220, 222 of the first PMB rotor 110. The rotor tube 240 separates the position sensing magnet 230 and the magnets 220, 222 of the first PMB rotor 110. A Hall Effect Sensor array (not shown in FIG. 2) is mounted in the controller 70 diametrically opposing the sensing magnet 230 and is used to monitor instantaneous longitudinal position of the rotor assembly 140. In some examples, the controller 70 and thus, the Hall Effect Sensor array is provided in the base of a mating pump module receptacle.

The Hall Effect Sensor's output, which is directly proportional to its instantaneous proximity to the permanent magnet 230 of the rotor assembly 140, is used to modulate the current in the VCA 120 such that the longitudinal position of the rotor assembly 140 remains in or close to its desired predetermined position. Operation of the VCA 120 for active longitudinal control/positioning of the rotor assembly 140 can interfere with the sensing magnet's 230 field, yielding a suboptimal signal-to-noise ratio. Thus, a compensation scheme may be employed in some implementations to mitigate this suboptimal signal-to-noise ratio. Determining rotor position is not limited to the sensing magnet 230 and Hall Effect Sensor arrangement. In other embodiments, rotor position may be determined using optical, ultrasonic, inductive, capacitive, and other position sensing methods.

In example embodiments, the VCA stator coil 250 is driven from a 24 VDC supply. The length of the VCA coil 250 was selected based on simulations that incrementally increased the length until sufficient force per square root of Watt was achieved. Selection of a larger wire diameters results in larger forces but also higher amounts of heat generation. The wire size may be selected based on an amount of heat that could be reasonably dissipated at the estimated average force that will be required from the VCA during normal operation. The following table lists characteristics of an example of the VCA design.

TABLE 1

| VCA Characteristics | | |
|---|---|---|
| Vs = | 24 | VDC |
| Wire Size | 23 | |
| Coil OD (in) | Coil ID (in) | Coil Len (in) |
| 1.58 | 1.18 | 0.5 |
| Total #turns | 160 | |
| Coil Resist | 1.2 | Ohms |
| Coil Inductance | .98 | mH |
| Current | 19.60 | ADC |
| Amp-Turns | 3136.1 | |
| Ave Force Constant | 1.6 | N/ADC |
| Heat at Max Amp-t | 470.4 | Watts |
| *Heat at 8.3N | 27.9 | Watts |

*Estimated Continuous Force over +/−.020 is 8.3N

Figure 8:
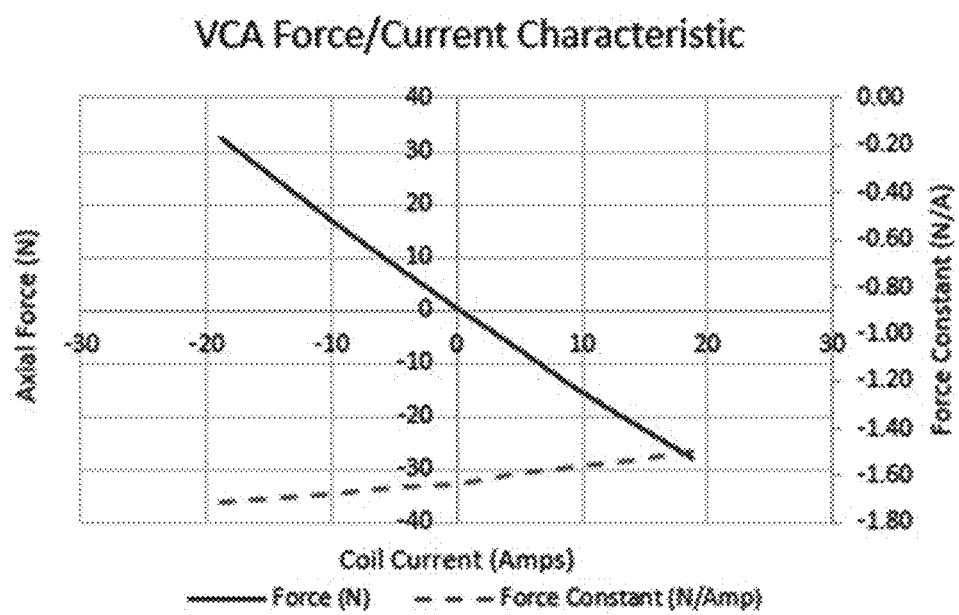
FIG. 8 is a chart showing VCA Force/Current Characteristic vs Axial Position from a magnetic analysis of the levitated motor shown in FIG. 2.

An example of VCA force generation as a function of coil current is shown in FIG. 8. In this simulation the rotor assembly 140 was centered axially, and the coil current varied up to a maximum of 3000 Amp—turns (almost 20 Amps). There are two curves in this plot. The solid line is the total force produced on the rotor assembly 140 as the VCA current is varied. The dashed line is the force constant of the VCA (Kf), which ideally is the constant of proportionality between the VCA current and force. The value of Kf, however, was not constant over the range of +/− current but varied from 1.71N/Amp at −18.75 Amps to 1.50N/Amp at +18.75 Amps.

The sensitivity of VCA force production to a radial displacement was also assessed by repeating the simulation at a radial offset of 0.010 inch as a check. The results showed that force produced by the VCA was not affected by the radial offset.

Figure 9:
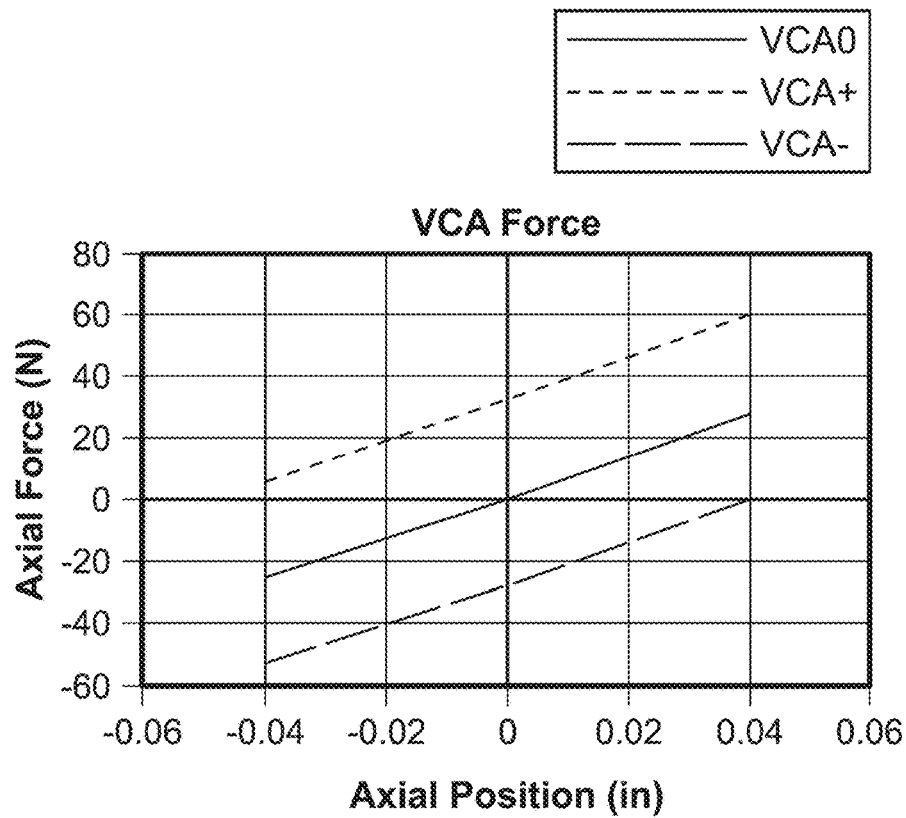
FIG. 9 is a chart showing a simulation of sensitivity of VCA force to Axial Position for the levitated motor shown in FIG. 2.
Figure 10:
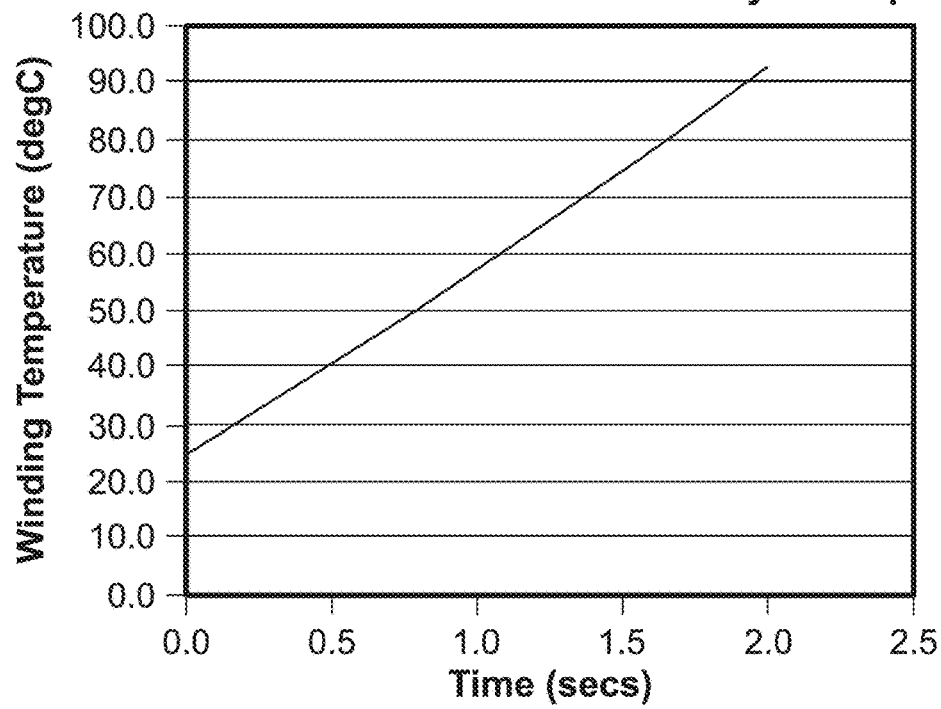
FIG. 10 is a chart showing VCA coil temperature during lift-off operation for the levitated motor shown in FIG. 2.

A simulation of sensitivity of VCA force to axial position is shown in FIG. 9 for one embodiment. In this case the total force on the rotor assembly 140 is the sum of the VCA force and the unstable axial forces that are primarily due to the interaction PMB rotors and stators. For stable operation criterion is that when the rotor assembly 140 is displaced to its maximum negative position the VCA can produce sufficient positive force to move the rotor assembly 140 back towards center. The maximum negative axial position offset occurs at startup and is 0.04 inch. By energizing the VCA with full current the rotor assembly 140 will be lifted off the startup position and then served around the zero position. Calculations of the VCA coil temperature during that lift-off operation show that the coil temperature will only increase 70° C. for 2 seconds of operation, (see FIG. 10). Typically, the rotor assembly 140 can be moved in milliseconds so the coil temperature should be much less than 70° C.

The active axial bearing 20 is not limited to a VCA. Other active axial bearing structures could include, for example, an arrangement of solenoidal coils and steel. Two solenoidal coils may be used, one to pull the rotor assembly 140 in a first longitudinal direction, and another to pull the rotor assembly in the opposite longitudinal direction.

Figure 11:
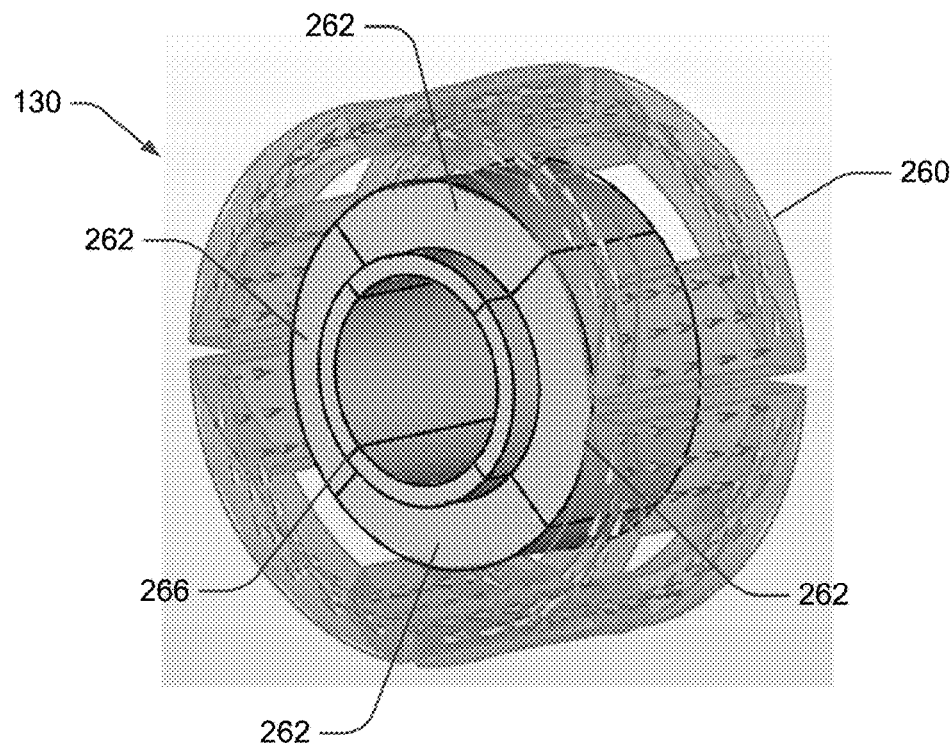
FIG. 11 is a cross section view illustrating aspects of an example of a brushless DC (BLDC) motor stator and rotor of the magnetically levitated motor shown in FIG. 2.

In the example shown in FIG. 2, the motor actuator 30 includes a slot-less brushless DC (BLDC) motor 130 to provide the desired rotational force on the rotor assembly 140. The motor actuator is not necessarily limited to a BLDC motor. For instance, a brushless AC (BLAC) or other motor structures could be used. The BLDC 130 satisfies torque-speed operating requirements within the voltage and current constraints specified for use in certain applications, such as an implantable and extracorporeal pump. In the illustrated example, the BLDC motor 130 includes a stator 260 with motor windings, and rotor magnets 262 mounted on a motor hub 266 that is attached to the rotor assembly 140. FIG. 11 illustrates further aspects of the stator 260 and rotor magnets 262 of an example of the BLDC motor 130.

In some examples, the BLDC motor 130 does not include a stator lamination stack as it can lead to high radial forces between the motor magnet and the lamination stack when either are not perfectly concentric. A four pole magnet design is used in some implementations based on size and volumetric efficiency. Two-pole designs have much longer coils since there are more turns of wire returning on the ends to be routed over the second pole. Comparatively, four-pole designs have half the number of turns over each pole so there is a smaller volume of copper that protrudes beyond the magnets. The principal motor characteristics for some examples are as follows:

Stator ID=1.18 inch
Rotor OD=1.0 inch
Rotor Magnet Length=0.40 inch
Overall Stator Coil Length=0.7 inch
Line to Line Electrical Characteristics: Resistance=4.1 Ohms; Inductance=0.280 mH; Torque Constant=0.0168; Nm/Apk Back Emf Constant=2.02 Vpk/krpm
Magnet Materials: NdFeB 45MGOe The weight of the rotor assembly 140 components is calculated as shown in Table 2. This does not include the weight of the plastic hub and impeller that these components are mounted to. It is assumed that the weight of those additional components is small compared to the weight of the magnets which have approximately the same density as steel.

TABLE 2

| Calculation of Rotor Mass Estimated Mass and Weight of Rotating Group | | | | |
|---|---|---|---|---|
| Dim | Motor | 2× PMB | Sensor | VCA |
| OD (in) | 1 | 1 | 0.6 | 1 |
| ID (in) | 0.54 | 0.54 | 0.44 | 0.54 |
| Length (in) | 0.54 | 0.18 | 0.18 | 0.5 |
| Mass (g) | 32.2 | 25.5 | 3.0 | 35.4 |

TABLE 2-continued

Calculation of Rotor Mass
Estimated Mass and Weight of Rotating Group

| Dim | Motor | 2× PMB | Sensor | VCA |
|---|---|---|---|---|
| Total Mass (g) = | 92.2 | | | |
| Total Weight (N) = | 0.90 | | | |

Figure 12:
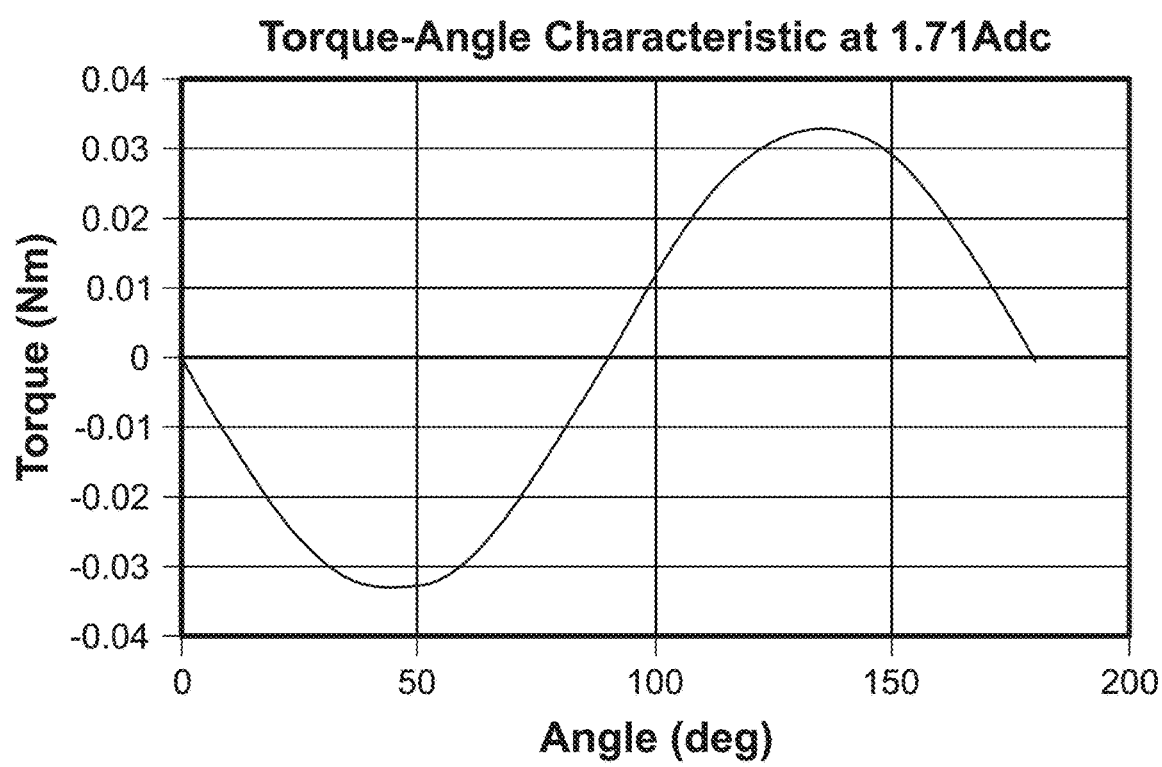
FIG. 12 is a chart showing a resulting waveform for one electrical cycle of the BLDC motor of the magnetically levitated motor shown in FIG. 2.

Torque performance of an example of the BLDC motor 130 was simulated for one electrical cycle with 1.71 ADC in the current (equivalent to a sinusoidally driven phase current of 1.97 Apk). The peak of the torque angle curve is 0.033 Nm. Therefore, the predicted torque constant is 0.0168 Nm/Apk. The implied back emf constant is 0.0193 V-s/rad (2.02 Vpk/krpm). FIG. 12 illustrates a resulting waveform that is very sinusoidal, which therefore produces smooth torque when run with a three-phase sinusoidal current drive.

Figure 13:
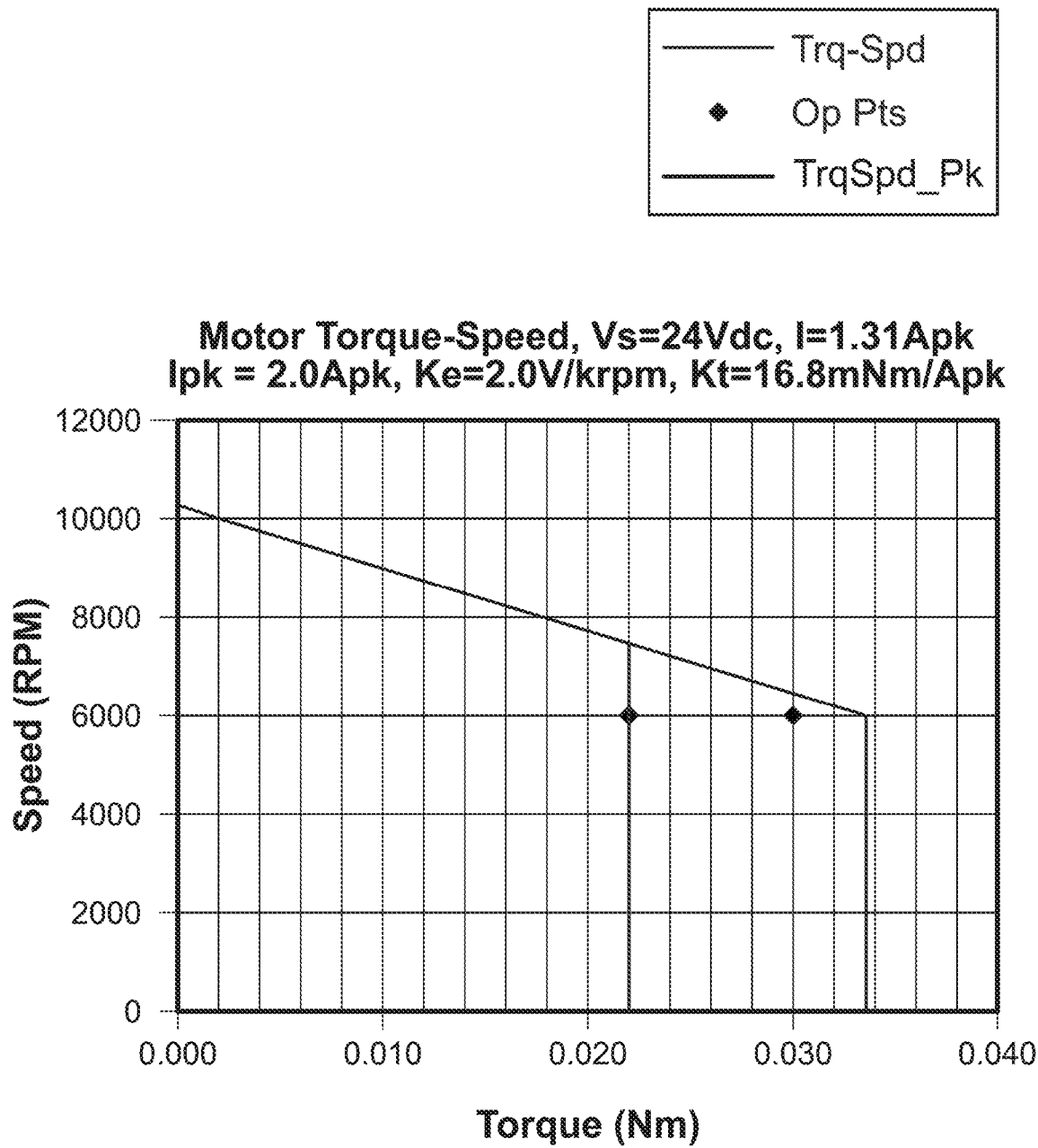
FIG. 13 is a chart showing steady state torque-speed characteristics of the BLDC of the magnetically levitated motor shown in FIG. 2 based on a an FEA analysis.

FIG. 13 illustrates characteristics of the BLDC 130 based on a an FEA analysis using motor design models as inputs to the torque speed simulation. The motor drive is assumed to use a standard sinusoidal drive to drive the motor winding current from a 24 VDC supply. As shown in FIG. 13, the BLDC 130 will produce 0.022 Nm up to a speed of 8200 rpm when the current is limited to 1.31 Apk. It can produce 0.034 Nm when the current limit is increased to 2.0 Apk.

The simulation shows that there is enough speed margin at an operating point of 0.022 Nm-6000 rpm to accommodate the typical+/−10% variation in motor characteristics parameters that can occur.

Figure 14:
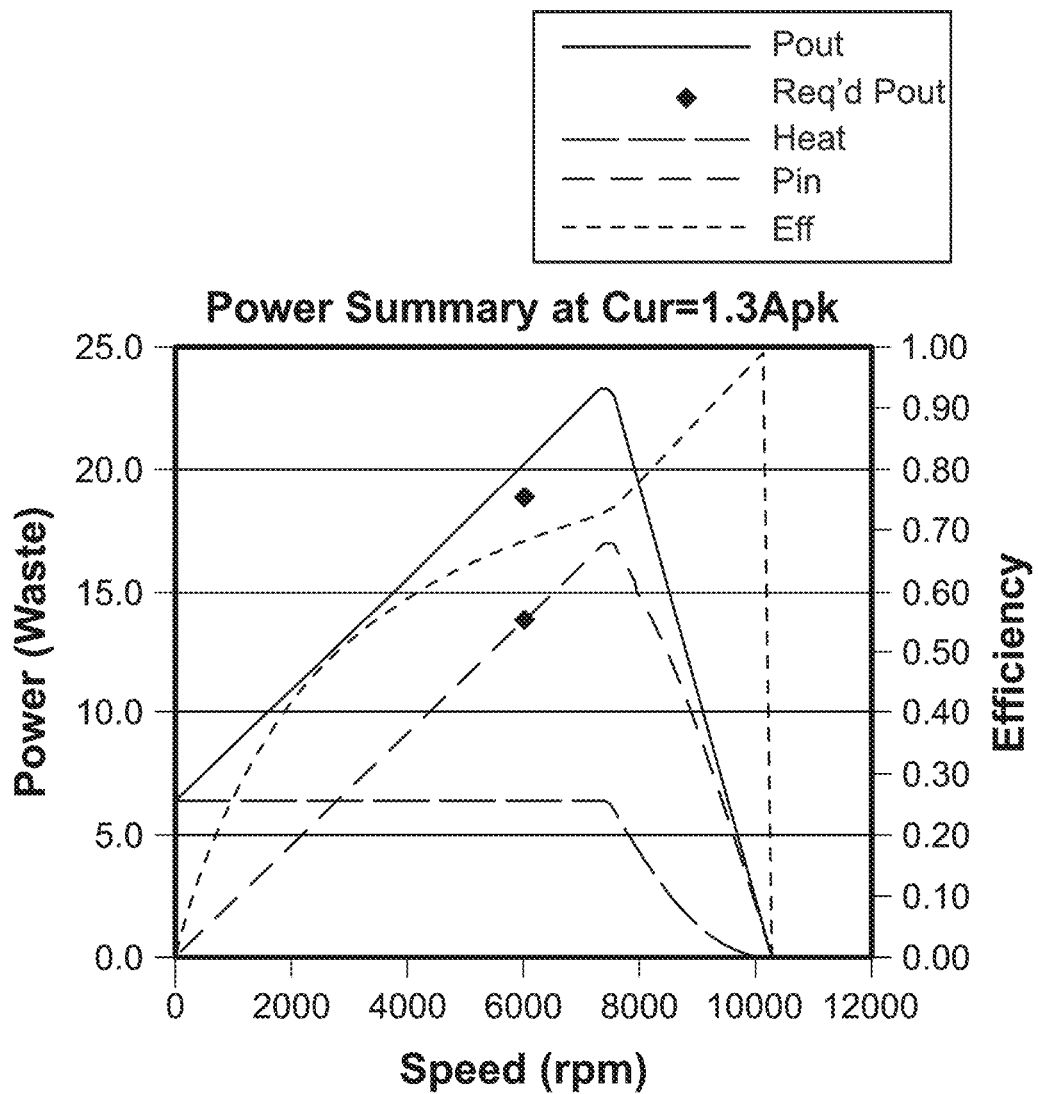
FIG. 14 is a chart showing a power summary for the magnetically levitate motor shown in FIG. 2.

A power summary is shown in FIG. 14, including the electrical input power required from the drive, (Pin); the mechanical output power delivered by the motor, (Pout); the motor efficiency; and the heat produced in the motor. For this simulation it was assumed that the motor winding current was 1.31 Apk and the winding temperature was 80° C. At these conditions the motor produces 6.4 Watts of heat. At the maximum current limit of 2.0 Apk the heat is 14.8 Watts.

Figure 15:
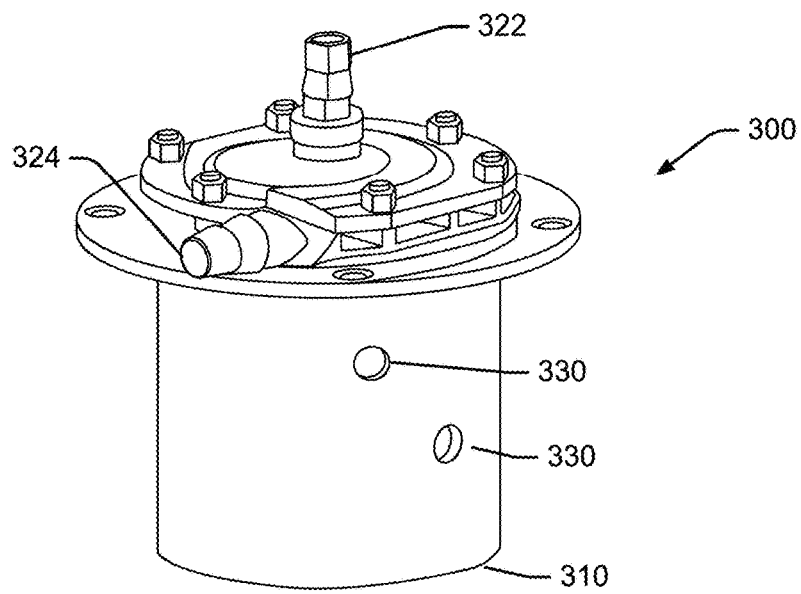
FIG. 15 is a perspective view illustrating an example of a pump system including an embodiment of a magnetically levitated motor in accordance with the present disclosure.
Figure 16:
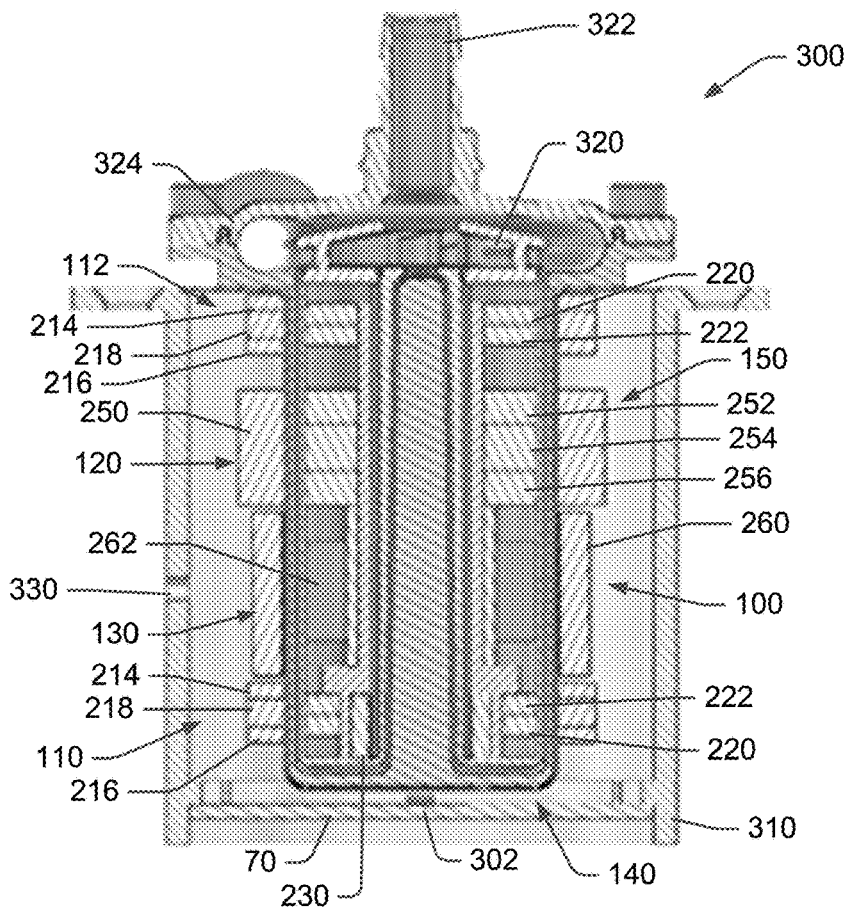
FIG. 16 is a cross section side view illustrating further aspects of the pump system shown in FIG. 15.

FIG. 15 is a perspective view, and FIG. 16 is a section side view illustrating an example of the motor 100 employed in a pump system 300. In some implementations, the pump system 300 is an implantable or extracorporeal blood pump. Such blood pumps may include an extracorporeal ventricular assist device (VAD) or an extracorporeal oxygenator. The stator assembly 150 and rotor assembly 140 of the motor 100 are received in a controller case 310. In some examples, the rotor assembly 140 and stator assembly 150 and associated components are all contained in case 310. In other examples, the rotating components (i.e. rotor assembly 140 and associated components) are contained in a pump module and the stationary components are contained in a pump housing, such as the case 310, into which the module is inserted. Therefore, the rotor assembly 140 and stator assembly 150 may be kept separate until time of use.

The case 310 includes openings 330 therethrough to provide access for cables. The motor 110 is in a vertical orientation, i.e. the motor axis extends vertically. A pump impeller 320 is positioned at a an upper, or first end of the case 310 and is connected to one end of the rotor assembly 140 adjacent the second PMB 112 such that the impeller 320 rotates with the rotor assembly 140.

A pump inlet 322 receives fluid, such as blood, which flows through the motor 100 between the rotor assembly 140 and stator assembly 150 and out through a pump outlet 324. In some examples, the inlet 322 and outlet 324 are barbed to facilitate connections to inlet and outlet tubing.

In some implementations, such as a blood pump, the motor 100 is configured to run over a speed range of 1000 RPM to 6000 RPM. The controller 70 is positioned at the lower end of the controller case 310, and includes a sinusoidal motor controller configured to control aspects of motor commutation and speed. A circuit board 302 is positioned at a lower, or second end of the case 310, and has the Hall Effect sensors mounted thereto as discussed above, with the sensing magnet 230 situated adjacent thereto.

Figure 17:
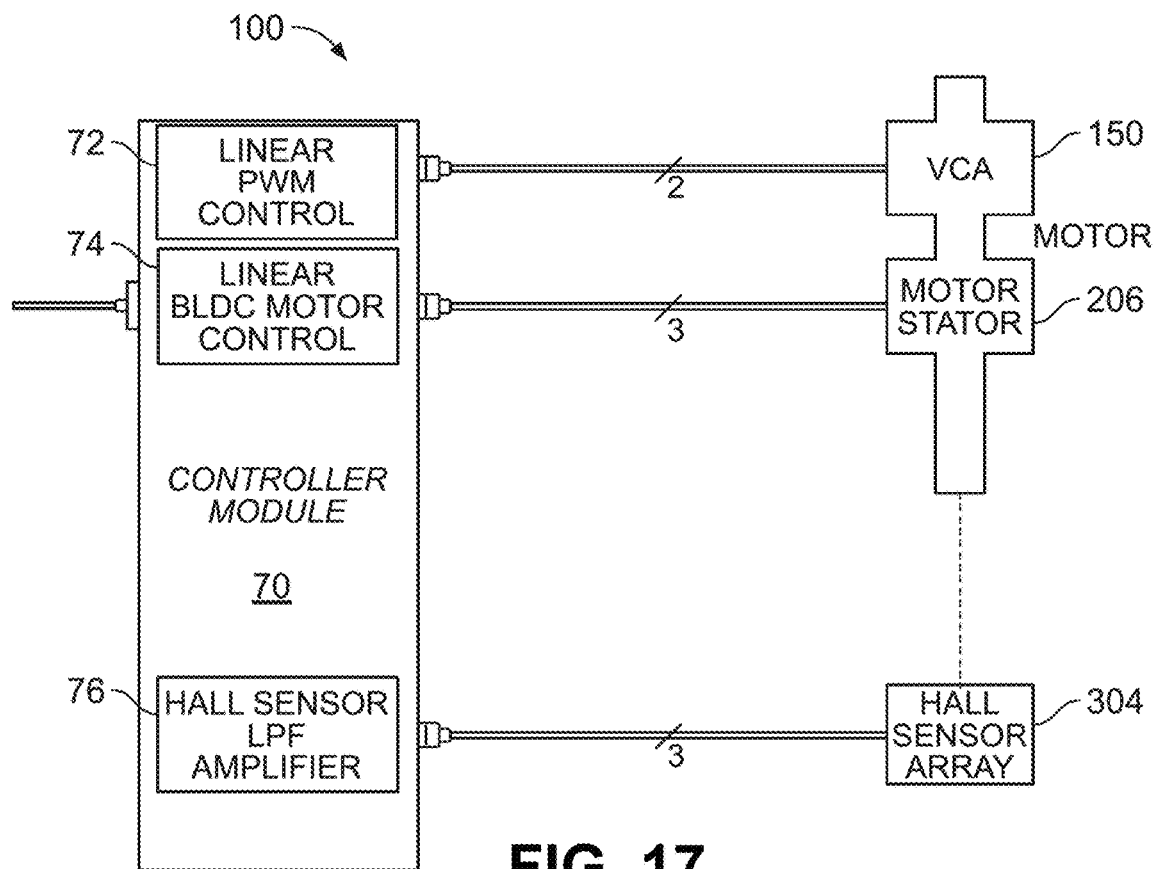
FIG. 17 is a block diagram illustrating an example of a motor controller in accordance with the present disclosure.

FIG. 17 is a block diagram illustrating an example of the controller 70, along with the motor 100 and Hall Effect Sensor array 304, which is mounted on the circuit board 302 as noted above. The controller 70 includes a linear PWM controller 72 connected to provide control signals to the VCA 120 for axial positioning of the rotor assembly 140. A BLDC motor controller provides control signals to the BLDC motor windings 260 to rotate the rotor assembly 140, and a Hall Sensor amplifier 76 receives signals from the hall sensor array 304 for determining radial and axial positions of the rotor assembly 140.

The Hall Sensor output, which is directly proportional to its instantaneous proximity to the sensing magnet 230, is used by the controller 70 to modulate the current in the VCA 120 such that the longitudinal position (i.e. vertical position in FIG. 15) of the rotor assembly 140 remains close to its ideal predetermined position.

Examples of the controller 70 have eight BNC connectors, with four pertaining to motor control and four pertaining to VCA control. A LabVIEW VI and COTS DAQ system with analog outputs for motor speed control and longitudinal position control and analog inputs for actual motor speed and rotor assembly 140 position are used in some implementations for overall control of the pump speed and longitudinal position.

As noted above, the sense magnet 230 is axially oriented and positioned into the bottom end of the rotor assembly 140 as shown in FIG. 15. The controller 70 includes a triad array of Hall Effect sensors mounted on the PCB 302 positioned to measure the axial component of flux density. The flux density varies with the axial position of the rotor assembly 140. The maximum flux density occurs when the rotor assembly 140 is "bottomed-out" and the fluid gap at the lower end of the controller case 310 is zero, e.g. at startup. The distance from the bottom of the magnet 230 to the Hall device sense area includes of the sections shown in Table 3 below. The total is approximately 4 mm (0.160 inch).

TABLE 3

Thicknesses of Sections between Magnet Bottom and Hall Sensor

| Section | Thickness (mm) | Thickness (in) |
|---|---|---|
| Bottom of rotating cup | 0.9 | 0.035 |
| Fluid Gap | 0.9 | 0.035 |
| Top of stationary cup | 1.5 | 0.059 |
| Hall to cup gap | 0.25 | 0.010 |
| Hall Sense plate in package | 0.41 | 0.016 |
| Total: | 3.96 | 0.16 |

In this example, the coordinate system was defined as having the position Z=0 coincident with the bottom of the magnet 230 when the rotor assembly 140 was positioned in the axially centered position. Therefore, flux density values probed and reported at Z=0.16 inch would coincide with the nominal position of the Hall sense area. Of course, the Hall Sensor board could be moved further away if necessary.

Figure 22:
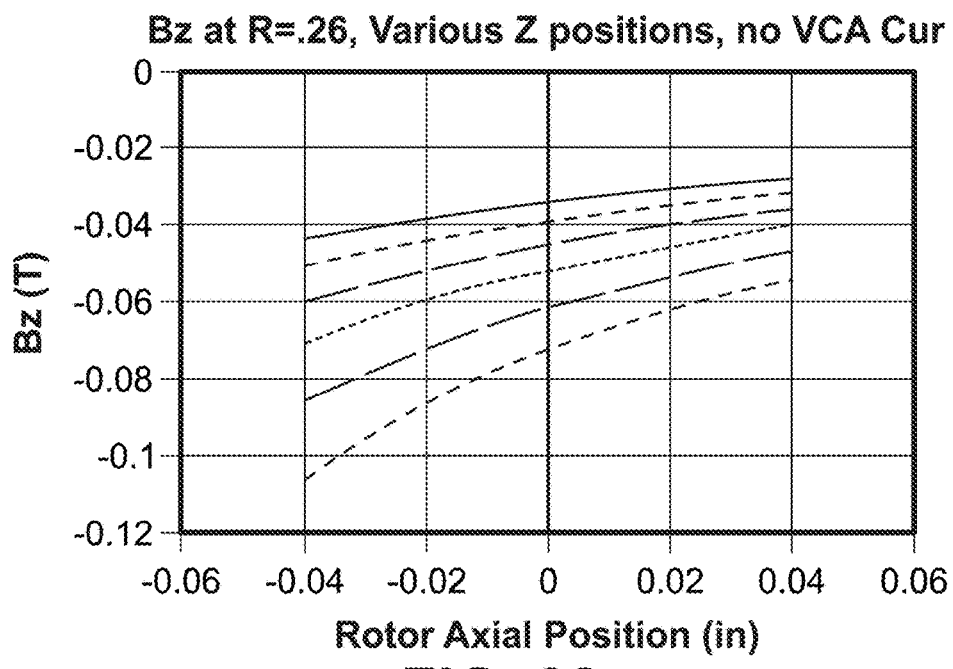
FIG. 22 is a chart showing Flux Density for various conditions the magnetically levitated motor shown in FIG. 2.

Analysis of the Flux density at various radial locations on the Z=0.16 inch (and other) planes showed that the maximum axial component of flux density occurred at a radius of 0.26 inch which is also the radial center of the sense magnet 230. Therefore, as the axial position of the rotor assembly varied from −0.040 to +0.040 inch, the flux density was probed only at a radius of 0.26 inch for six different possible axial locations of the Hall Sensor (z=0.15 inch to z=0.25 inch). The results are shown in FIG. 22. The axial movement of −0.04 inch to +0.04 inch was selected as representative of the operating region of the rotor assembly 140. The starting "bottomed-out" position is −0.036 inch. Ideally, once the pump has lifted off the operating position will be confined to +/−0.020 inch around the defined axially centered position.

Figure 23:
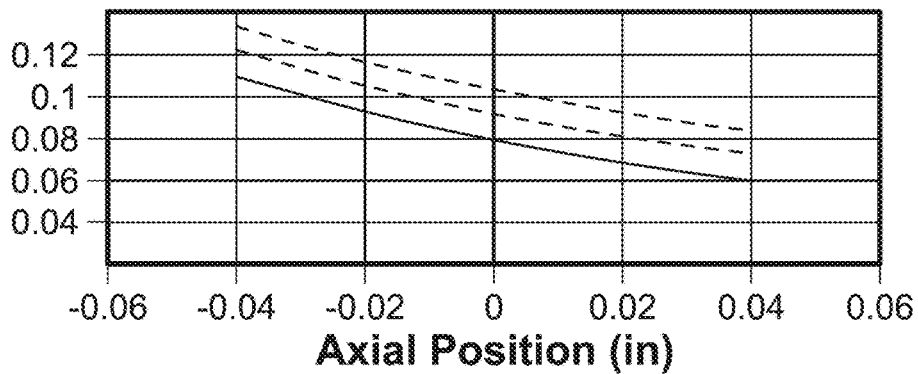
FIG. 23 is a chart showing Flux Density for further conditions of the magnetically levitated motor shown in FIG. 2.

The influence of the VCA current has on the sensed flux density was analyzed at +/− full VCA current, (See FIG. 23). This analysis was based on an axial location of the sense element of 0.17 inch which includes a little extra space for assembly and or manufacturing clearances. The contribution due to the VCA varies from 0.011 Tesla to 0.012 Tesla over the range of positions analyzed. This is approximately 18% of nominal value of 0.6 Tesla at the aligned position. It is an even larger percentage at a location of z=0.02 inch.

Figure 24:
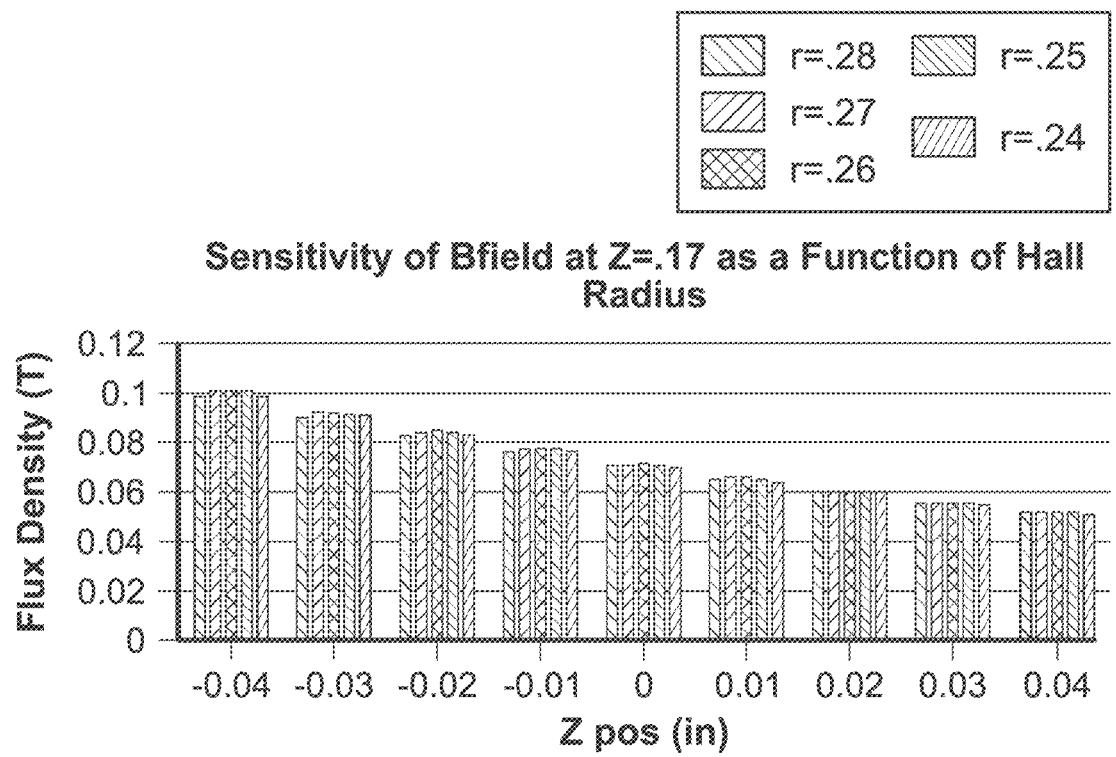
FIG. 24 is a chart showing a sensitivity analysis of the sensed B-field as a position of Hall Effect devices of the magnetically levitated motor shown in FIG. 2.

A sensitivity analysis of the sensed B-field to the position of the Hall devices was also performed. In the plot shown in FIG. 24 the bars show the B-field at slight variations of +/−0.01 inch and 0.02 inch in sensor radius. The groups of bars correspond to different axial positions of the rotor assembly 140 as it varies from −0.04 inch to +0.04 inch from the nominal aligned position.

An example radial force summary is shown in Table 4 below. Given the nominal forces predicted via various simulations and calculations at an assumed operating radial displacement of 0.01 inch, there is still a net radial restoring force. This means that the actual operating radial displacement would be less. However, if we assume a 25% worst case error on all source forces the net available restoring force would be zero and therefore the operating radial displacement would be 0.01 inch as assumed.

TABLE 4

Running Radial Force Summary
Force Summary at Axial Displacement of .02 inch
Summary of Radial Forces at Worst Case Radial Displacement of .01"

| Source | Nominal F_Radial (N) | Error Analysis (Assumed Error) |
|---|---|---|
|  |  | 0.165 |
| Rotating Group | −3.19 | −2.66 |
| Impeller (Hydraulic) | 1.91 | 2.23 |
| Rotating Group Imbalance | 0.38 | 0.444 |
| Total | −0.9 | 0 |

An axial force summary is given in Table 5 below. This table summarizes the expected forces over the estimated operating range of +/−0.020 inch. Given the average VCA force constant of 1.6N/Amp the required VCA current at the endpoints of the operating range would be 8.8 Amps. Assuming that during operation the axial position varies linearly over the range the rms force output of the VCA would be 8.4N. This is close to the initial estimate made in the table below and therefore the estimated average heat generated in VCA would be 28 Watts.

TABLE 5

Running Axial Force Summary
Summary of Axial Forces at Radial Displacement of .01"

| Source | −.020 Axial Disp F_Axial (N) | +.020 Axial Disp F_Axial (N) |
|---|---|---|
| Rotating Group | −11.2 | 16.7 |
| Hydraulic | 2.03 | 2.03 |
| Rotating Group Weight | −1 | −1 |
| Total | −10.2 (= 6.3 A) | 17.7 (= 10.9 A) |

A startup force summary was also performed and given in Table 6 below. This table summarizes the expected forces at an axial position of −0.040 inch which is the startup "bottomed-out" position. We see that the total force that would need to be overcome by the VCA would be 26.1N. This would require a VCA current of 15.3 Amps which is within the limits of the device.

TABLE 6

Startup Force Summary
Summary of Axial Forces at Radial Displ. of .01"

| Source | −.040 Axial Disp F_Axial (N) |
|---|---|
| Rotating Group | −25.1 |
| Hydraulic | 0 |
| Rotating Group Weight | −1 |
| Total | −26.1 |

Figure 18:
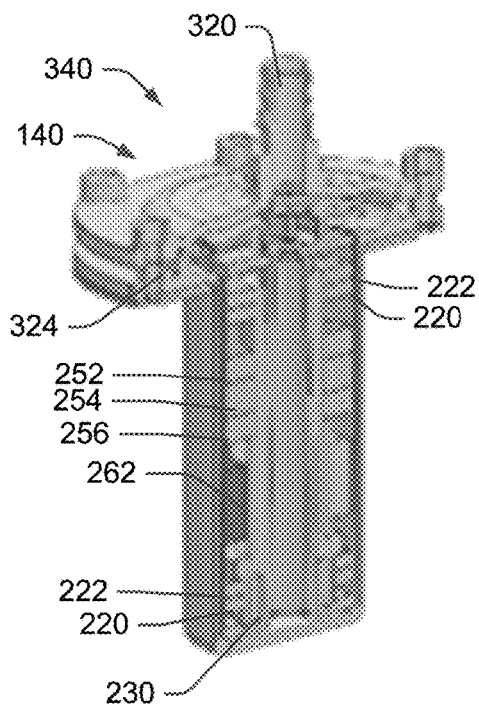
FIG. 18 is a cross section side view illustrating an example of portions of a pump module in accordance with the present disclosure.
Figure 19:
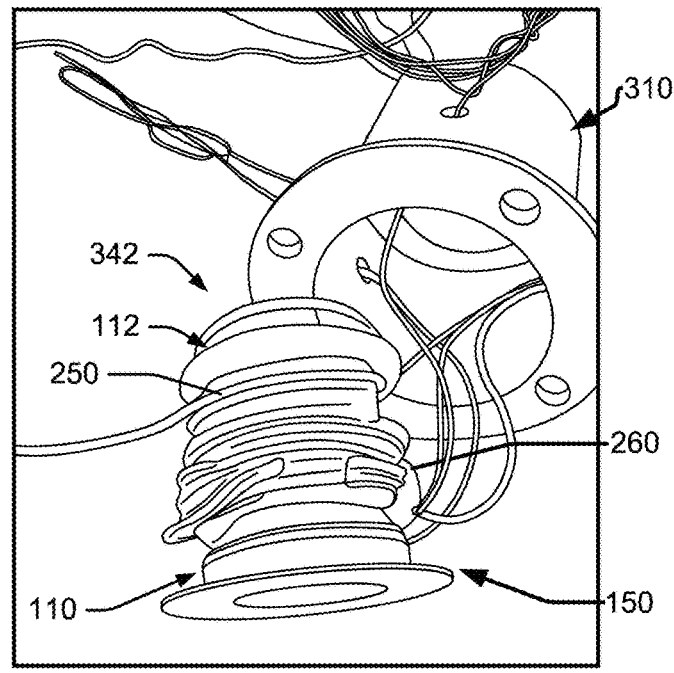
FIG. 19 is a perspective view illustrating an example of a pump module in accordance with the present disclosure.

As noted above, some embodiments include a pump module housing the rotating components of the pump system 300 (i.e. rotor assembly 140 and associated components), while the stationary components are contained in a pump housing, such as the case 310, into which the module is inserted. FIG. 18 illustrates a pump module 340 that contains the rotor assembly 140 with the impeller 320 attached thereto. FIG. 19 illustrates and example of a pump housing 342 having the stator assembly 150 mounted thereon, which is configured to receive the pump module 340. The pump housing 342 and module 340 are mounted in the case 310.

Figure 20:
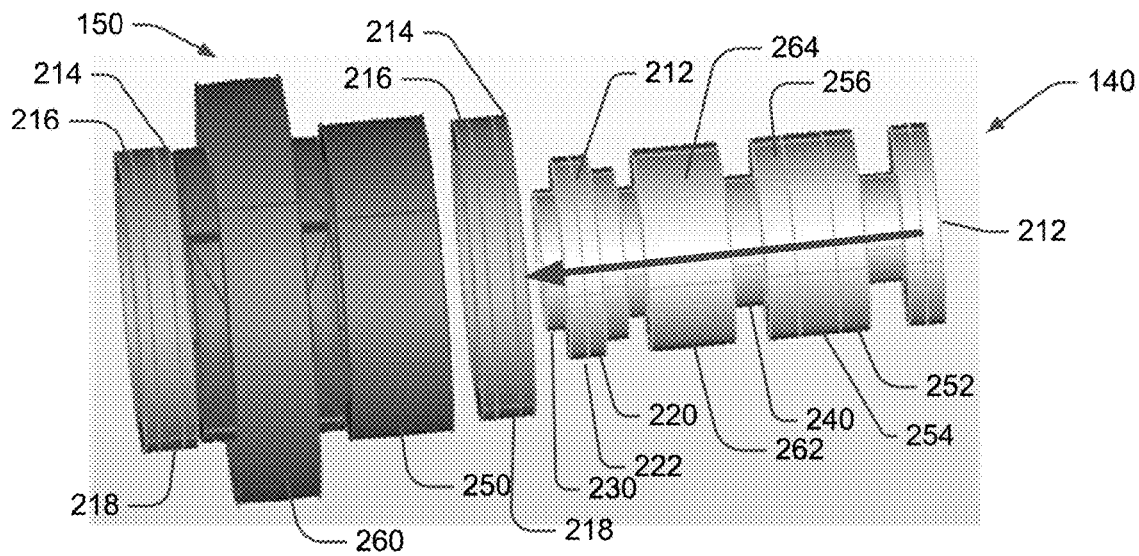
FIG. 20 is a side view conceptually illustrating a rotor assembly being inserted into a stator assembly in accordance with the present disclosure.

FIG. 20 illustrates the rotor assembly 140 being inserted into the stator assembly 150 from right to left. When the rotor assembly 140 (including the rotor tube 240, the PMB rotor 212, the PMB magnets 220, 222, the VCA rotor magnets 252, 254, 256, BLDC rotor magnets 262, BLDC hub 266, and sensing magnet 230) is inserted into the stator assembly 150 (including the PMB magnets 214, 216 and the PMB spacers 218, the VCA winding 250, and the BLDC stator 260), the rotor assembly 140 will experience both positive and negative axial forces as the different magnets on the rotor assembly 140 pass through the various magnets on the stationary members of the stator 50.

Figure 21:
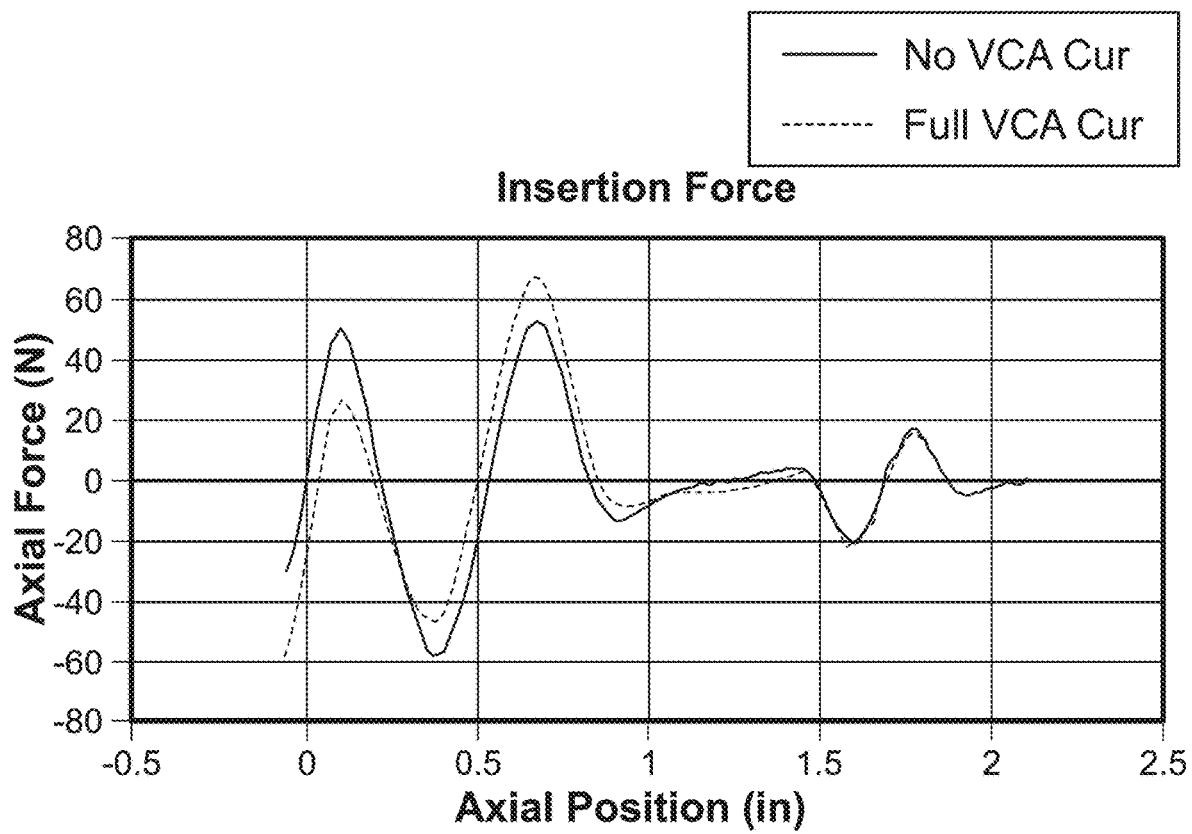
FIG. 21 is a chart showing a simulation of insertion forces for the rotor and stator shown in FIG. 20.

A simulation of insertion forces is shown in FIG. 21. The solid line is with the VCA 120 unenergized. For this plot, the axial position of zero is defined as when the rotor assembly 140 is fully inserted and axially centered in the stator assembly 150. In the illustrated example, at the start of the insertion process the rotor assembly is at an assumed position of z=2.1 inch. There is a small+/− axial force variation as the first PMB rotor 212 and sense magnet pass 230 through the first PMB 110 stator 210. There is an even smaller+/− axial force that occurs as the BLDC magnets 262 pass through the first PMB 110 stator 210. Next there is a large+/− axial force as the VCA magnets 252, 254, 256 pass through the first PMB 110 stator 210. Lastly there is another large+/− axial force as the first PMB 110 and second PMB 112 rotor magnets 220, 222 pass through the first and second PMB stator magnets 214, 216 respectively. As the rotor assembly 140 is driven through the zero axial position there is a negative axial force which will hold the rotor assembly 140 in a "bottomed-out" position. Also shown in FIG. 21 is the insertion force with the VCA 120 energized at full current. More "bottomed-out" holding force can be attained by energizing the VCA 120.

As noted above, an example of the controller 70 includes a sinusoidal motor controller. Embodiments of the sinusoidal motor controller utilize a highly integrated three-phase sensorless motor driver with integrated power MOSFETs which can provide continuous drive currents of 2 Amperes and peak currents to 3 Amperes. The motor controller uses a sensorless control and feedback scheme to provide continuous sinusoidal drive which significantly reduces the pure tone acoustics that typically occur as a result of trapezoidal commutation.

The device is configurable through a digital serial interface to accommodate different motor parameters and alignment, open-loop ramp-up, and closed-loop control profiles for different applications. A 180° sensorless control scheme provides continuous sinusoidal output voltages to the motor phases to enable ultra-quiet motor operation by minimizing the electrically induced torque ripple. Extensive protection and fault detect mechanisms are included to ensure reliable operation. Voltage surge protection prevents the power supply input Vcc capacitor from overcharging, which is typical during motor deceleration. The devices provide overcurrent protection and rotor lock detection through several methods. These methods can be configured with internal register settings to ensure reliable operation. The device provides additional protection for under-voltage lockout (UVLO) and for thermal shutdown. The commutation control algorithm continuously measures the motor phase current and periodically measures the motor supply voltage (Vcc). The device uses this information for BEMF estimation, and the information is also provided through the digital register interface for debug and diagnostic use in the system if desired. A TTL compatible digital TACH output signal corresponding to the motor commutation frequency is provided as the speed indicator output.

An EEPROM integrated into the motor controller, for example, is used as memory for the motor parameters (e.g. Rmotor, Ke, etc.) and operation settings including slew rate control.

The output voltage amplitude applied to the motor is accomplished through sine wave pulse width modulation such that the resulting phase-to-phase voltage is sinusoidal. When a phase is measured with respect to ground the resulting waveform is sinusoidally coupled with third-order harmonics. This encoding technique permits one phase to be held at ground while the other two phases are pulse-width modulated. Constant speed control of the three-phase pump motor, under varying or pulsatile load conditions, is achieved by varying the amount of current delivered to the stator windings proportionally to the motor's load.

The voltage output amplitude of each phase is determined by the magnitude of the system supply voltage Vcc and the commanded PWM duty cycle output. The PWM output may vary from 0 to 100% resulting in an output amplitude of 0 VDC to Vcc. Variations in differential pressure across the pump will impart instantaneous changes in the pump's speed. The motor controller will sense this change in speed through its back-EMF sampler and attempt to speedup or slow down the pump such that the preset speed is maintained. This instantaneous load change and corresponding correction performed by the motor controller will result in a corresponding variation in the pump's current (power), speed, and flow waveforms. An instantaneous increase in the pump's load will cause an instantaneous decrease in pump speed and thus an instantaneous increase in pump current (power) and decrease in flow rate. Conversely, an instantaneous decrease in the pump's load will cause an instantaneous increase in pump speed and thus an instantaneous decrease in pump current (power) and increase in flow rate.

Therefore, the pump's current (power), speed, and flow waveforms correlate well with changes in the pump's load. These waveforms are rich in information and may be used to calculate the patient's pulse rate, instantaneous and mean blood flow rate, regurgitant flow, instantaneous and mean power consumption, the pump's efficiency, and more.

The sine wave generated in the motor controller's lookup table can be very pure, and this will translate into an equivalent PWM voltage which is also pure. However, when operating the motor at maximum speed, the sine waves peaks reach the bus voltage rails. When one phase is at a positive peak, the other two phases are at a negative value of only one-half the negative peak (with respect to the midpoint of the bus voltage, where the duty would be at 50%, the middle of the sine waves are centered here). The same is true for the negative peaks, the one phase is at the negative rail, but the other two phases are not at the plus rail. This means that at any moment, we cannot fully use the available bus voltage to allow the real maximum speed at the motor. There are a few methods to deal with this. One method is the Space Vector modulation approach, which basically sets one phase at a time equal to a bus rail, and pivots the other two phases around it, until one of the other phases reaches the rail, then the pivot switches to that phase, and it works its way around to both rails on all three phases. This utilized the whole bus voltage, but requires the algorithm to detect which phase is stationary, and which phases are pivoting. Also, the Space Vector approach uses 100% modulation on the pivot phase, which means that some gate driver chips may experience a time without a voltage refresh, especially at lower speeds. Another method is the method of third-harmonic injection (which Texas Instruments uses in the DRV10983). In this method, the only thing that differs from the standard sine lookup table is that the sine table has a third harmonic component added to the fundamental sine component. The amplitude of the third-harmonic component is one sixth that of the fundamental. The resulting waveform looks somewhat flattened, as the peaks of the harmonic and the peaks of the fundamental are opposite in polarity, so the normally rounded peak of the sine is dipped down slightly. The motor phases have the modified sine wave on each phase signal and are 120-degrees apart. Each phase has the same third harmonic which, after the 120 and 240-degree index offsets, have the same amplitude and phase. The resulting phase-to-phase voltage is a clean sine wave, because the third harmonic component is entirely canceled out. What is more important for us is that each phase is now centered within the bus rails better, so that we can now utilize 16% more of the bus voltage for motor control than we could without the added harmonic. Since some motor applications (i.e. pediatric blood pumps) must run at higher speeds this is a tremendous benefit with lower system voltages. The benefit is higher speed capability, which can be utilized without any penalty in processor demand. The only difference in using this over the pure sine version is in the data loaded into the sine lookup table read to determine the sinusoidal wave form, and in the scaling of the voltage command limiter.

Referring back to FIG. 17, in one implementation the Hall Sensor Array 304 includes three Hall Sensors whose active elements are configured in a 0.26 inch circle (diameter of circular magnet's midline) and phased 120° from each other. The voltage output of the magnetic sensor 76 is directly proportional to the proximity of the permanent magnet 230 in the rotor assembly 140 to the top surface of the array 304. The individual sensor outputs are then averaged and low pass filtered to ensure that a single stable output voltage proportional to the longitudinal position of the rotor assembly 140 is generated and fed to the longitudinal position control system 72 for processing. This signal may be synchronously sampled by the longitudinal position control system 72 during the off time of the PWM signal driving the VCA 120. This is done to further minimize undue influence of the VCA's magnetic field onto the permanent magnet's field.

The VCA driver output stage in some examples utilizes two half H-Bridge Drivers (Infinion BTS7960) configured as a full H-Bridge driver output stage and PWM frequencies between 10 kHz and 50 kHz may be selected for use. The actuator's PWM frequency should be high enough such that it is sub-audible but low enough such that it provides linear duty cycle control over the desired current operating range. Due to the coil's relatively high inductance sub-audible control will be achievable in the nonlinear region. The maximum usable PWM frequency for non-linear duty cycle control will be dependent upon the maximum average current needed to modulate the position of the rotor assembly 140 such that it is in the ideal position for radial stability.

Figure 25:
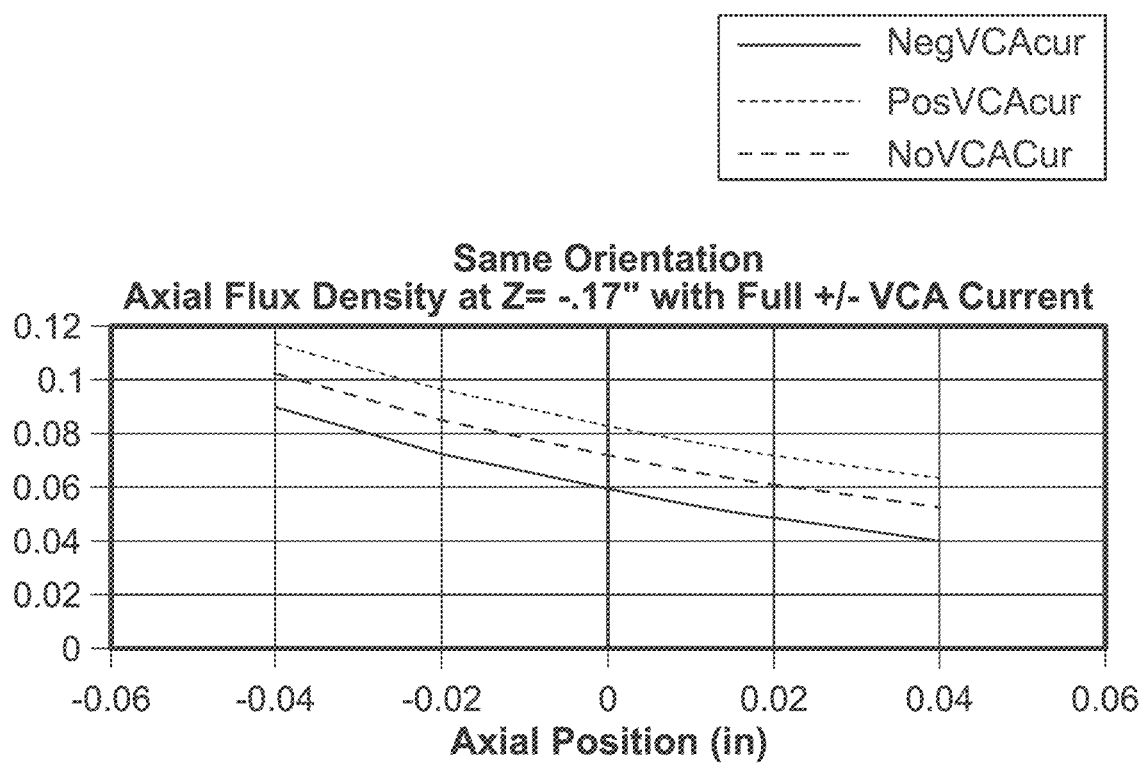
FIG. 25 is a chart showing Axial Flux Density for certain conditions of the magnetically levitated motor shown in FIG. 2.

In the exemplary design, the influence of the VCA current has on the sensed flux density was analyzed at +/- full VCA current as shown in FIG. 25. This analysis was based on an axial location of the sense element of 0.17 inch which includes space for assembly and/or manufacturing clearances. The contribution due to the VCA varies from 0.011 Tesla to 0.012 Tesla over the range of positions analyzed. This is approximately 18% of nominal value of 0.6 Tesla at the aligned position. It is an even larger percentage at a location of z=0.02 inch.

The sense magnet 230 orientation was made to be the same direction as the PMB magnets 262. This results in a better sensitivity. In this case, the VCA's magnetic field contribution and its resulting positional uncertainty are dealt with to avoid potential positive feedback in the rotor assembly 140 longitudinal position closed-loop feedback control system, further resulting in oscillatory position control and instability. From the graph of Axial Flux Density versus VCA shown in FIG. 25, it is noted that the undue effects of the VCA current and resulting magnetic field are quasi-linear over the exemplary embodiment's longitudinal position control range of −0.04 inch to +0.40 inch. Since the instantaneous magnetic field strength of the VCA is proportional to VCA drive current and the VCA drive current is proportional to the instantaneous pulse width of the driver signal, the PWM signal itself may be used to offset or negate the undue magnetic field contribution of the VCA. In this way, the instantaneous PWM driver input signal is low-pass filtered to yield an analog voltage signal proportional to VCA drive current. This analog signal is then used as a scalar multiplier to compensate the magnetic sensor's output signal and negate the influence of the VCA magnetic field.

Figure 26:
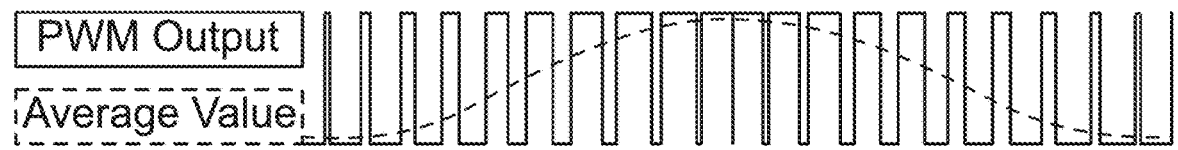
FIG. 26 is a chart showing an analog compensation signal for the magnetically levitated motor shown in FIG. 2.
Figure 27:
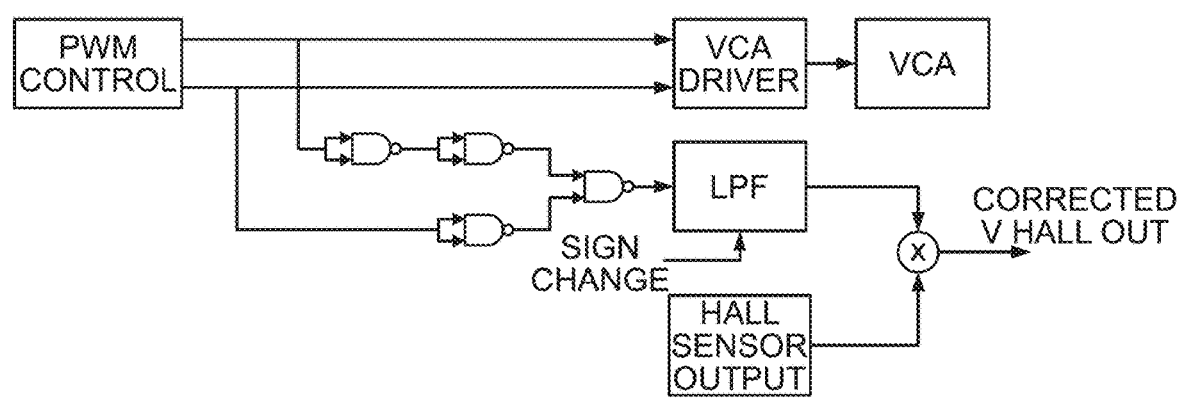
FIG. 27 is a block diagram of an example VCA Magnetic Field Offset Compensation Circuit in accordance with disclosed embodiments.

An analog compensation signal proportional to the instantaneous pulse width of the VCA driver control signal is shown in FIG. 26, and a Block Diagram of an example VCA Magnetic Field Offset Compensation Circuit is shown in FIG. 27.

Figure 28:
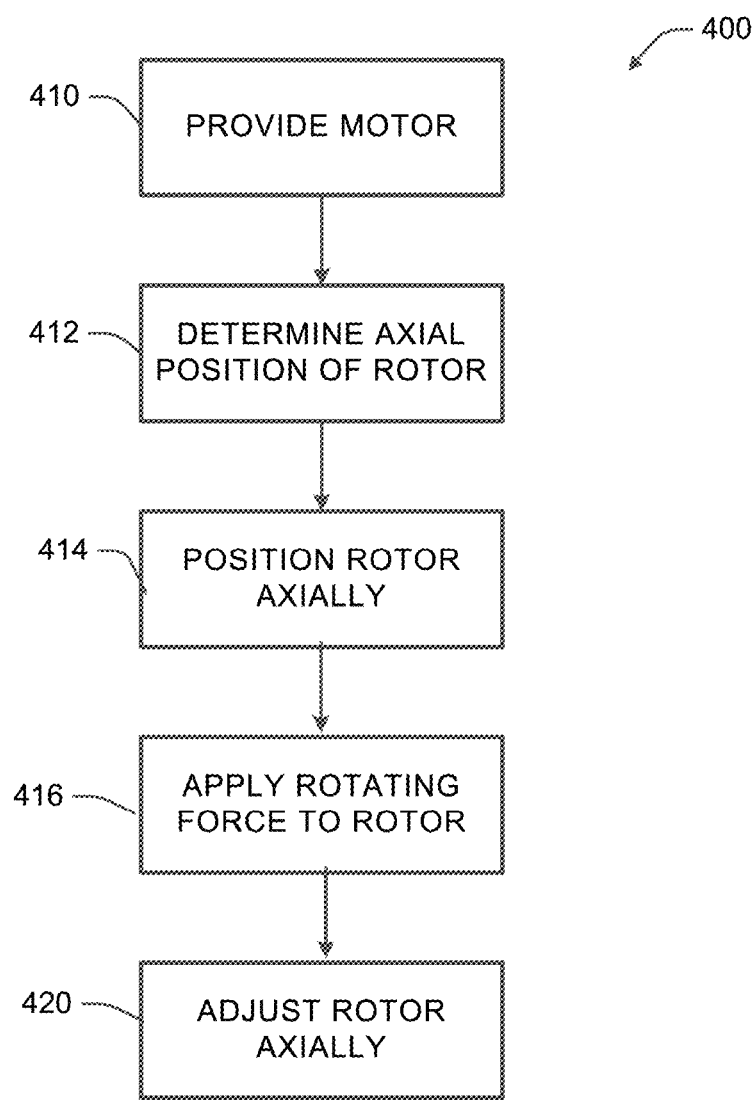
FIG. 28 is a flow diagram illustrating a motor operation method in accordance with the present disclosure.

FIG. 28 is a flow diagram illustrating a motor control method 400 in accordance with some disclosed embodiments. In an operation 410, a motor such as the magnetically levitated motor 100 shown in FIGS. 1 and 2 is provided. The motor includes the stator 50, rotor 40 configured to rotate relative to the stator 50. The rotor 40 is supported radially by the passive radial magnetic bearings 10, 12. In operation 412, an axial position of the rotor relative to the stator is determined. As noted above, in some examples this is accomplished by the Hall Effect Sensors determining the position of the sensing magnet 230. The active longitudinal magnetic bearing 20 is activated to selectively modify the axial position of the rotor relative to the stator in response to the determined axial position in operation 414. In some examples, this results in moving the rotor axially from a bottomed out position, where the rotor is resting on a surface of a pump or motor case. Thereafter, in operation 416, a rotating force is applied to the rotor to rotate the rotor relative to the stator.

In operation 420, after applying the rotating force in operation 416, the active longitudinal magnetic bearing is activated to further modify the axial position of the rotor such that the rotor is radially stabilized by the passive radial magnetic bearings. In other words, once the motor is operating, the active longitudinal magnetic bearing is activated to position the rotor in the axial direction to stabilize the radial position of the rotor by the passive radial magnetic bearings.

Thus, disclosed embodiments provide a blood pump that combine an electric motor and magnetic levitation system that allows a rotor/impeller assembly to be suspended in the blood in a contactless manner. Passive static magnetics provide a radial bearing system. Due to physics regarding creation of a completely static/passive stable magnetic levitation system in all three dimensions, (refer to Earnshaw's Stability Theorem), an active longitudinal magnetic bearing employing a VCA controls the axial position of the floating/rotating assembly of components. The VCA is part of a position feedback system that senses the axial position of the floating pump assembly via Hall effect sensors. The feedback system varies the current in the VCA coil to produce an axial magnetic force acting on the moving assembly and controlling its position. A BLDC motor provides torque-speed operating requirements within desired voltage and current constraints. The BLDC motor has no cogging torque and will apply smooth torque to the rotating pump group.

In accordance with disclosed examples, the longitudinal displacement of the magnetically levitated rotor is actively modulated to be maintained at a position such that it is radially stabilized by the two passive magnetic bearings. The PMBs may be optimized to minimize the ratio of axial to radial force production, monitoring the instantaneous longitudinal position of the rotor and using this measurement to servo the rotor to a predetermined position such that the passive radial bearings provide adequate radial stability to the rotor. The permanent magnet sense magnet provides a magnetic field to measure the rotor's instantaneous position. The south pole downward facing arrangement of the sense magnet provides a magnetic field to measure the rotor's instantaneous position while increasing the sensor's signal-to-noise (SNR) ratio and minimizing the effects of extraneous magnetic fields produced within the motor.

Various modifications and alterations of this disclosure may become apparent to those skilled in the art without departing from the scope and spirit of this disclosure, and it should be understood that the scope of this disclosure is not to be unduly limited to the illustrative examples set forth herein.

What is claimed is:

1. A device, comprising:
   a stator;
   a rotor configured to rotate relative to the stator;
   a passive radial magnetic bearing configured to support the rotor relative to the stator in a radial direction, the passive radial magnetic bearing comprising:
      a passive magnetic bearing (PMB) stator including a first PMB stator magnet and a second PMB stator magnet attached to the stator and arranged in a bucking configuration, with a non-magnet spacer situated between the first PMB stator magnet and the second PMB stator magnet, PMB stator magnet are permanent magnets; and
      a PMB rotor including a first PMB rotor magnet and a second PMB rotor magnet attached to the rotor and arranged in a bucking configuration, wherein the PMB rotor magnet and the second PMB rotor magnet are permanent magnets; and
   an active longitudinal magnetic bearing configured to selectively position the rotor relative to the stator in an axial direction.

2. The device of claim 1, further comprising:
   an actuator configured to selectively generate a rotating force to rotate the rotor relative to the stator.

3. The device of claim 2, wherein the actuator comprises a slot-less brushless DC (BLDC) motor, the BLDC motor including:
   a BLDC motor magnet attached to the rotor; and
   a BLDC motor winding surrounding the BLDC motor magnet.

4. The device of claim 3, wherein the BLDC motor magnet includes a four pole magnet design.

5. The device of claim 2, further comprising:
   a position sensing magnet attached to the rotor; and
   a motor controller including a Hall Effect Sensor array configured to determine a position of the rotor relative to the stator based on the position sensing magnet.

6. The device of claim 5, further comprising:
   a case having a first end and a second end, wherein the stator, the rotor, the passive radial magnetic bearing, the active longitudinal magnetic bearing, and the position sensing magnet are received in the case;
   an impeller attached to the rotor at the first end of the case;
   a circuit board having the Hall Effect Sensor array mounted thereon, the circuit board mounted at the second end of the case adjacent the sensing magnet.

7. The device of claim 6, wherein the Hall Effect Sensor array includes Hall Effect Sensors arranged in a circular array on the circuit board positioned circumferentially around a rotational axis of the rotor.

8. The device of claim 5, wherein the actuator is positioned between the position sensing magnet and the active longitudinal magnetic bearing in the axial direction.

9. The device of claim 1, further comprising:
   a motor controller configured to output control signals to the active longitudinal magnetic bearing to selectively position the rotor relative to the stator in the axial direction.

10. The device of claim 1, wherein the passive radial magnetic bearing includes a first passive magnetic bearing and a second passive magnetic bearing positioned at respective first and second ends of the rotor.

11. The device of claim 1, wherein the active longitudinal magnetic bearing comprises a voice coil magnetic actuator (VCA).

12. The device of claim 11, wherein the VCA comprises:
   a VCA rotor magnet connected to the rotor; and
   a VCA winding extending around the VCA rotor magnet.

13. The device of claim 12, wherein the VCA rotor magnet comprises:
   a first VCA rotor magnet and a second VCA rotor magnet arranged in a bucking configuration; and
   a third VCA rotor magnet positioned between the first VCA rotor magnet and the second VCA rotor magnet, the third VCA rotor magnet including a plurality of 90 degree segments magnetized in a radial orientation.

14. A device, comprising:
   a stator;
   a rotor configured to rotate relative to the stator;
   a passive radial magnetic bearing configured to support the rotor relative to the stator in a radial direction, the passive radial magnetic bearing comprising:
      a passive magnetic bearing (PMB) stator including a first PMB stator magnet and a second PMB stator magnet attached to the stator and arranged in a bucking configuration, with a non-magnet spacer situated between the first PMB stator magnet and the second PMB stator magnet; and
      a PMB rotor including a first PMB rotor magnet and a second PMB rotor magnet attached to the rotor and arranged in a bucking configuration; and
   an active longitudinal magnetic bearing configured to selectively position the rotor relative to the stator in an axial direction, wherein the active longitudinal magnetic bearing comprises a voice coil magnetic actuator (VCA) comprising:
      a VCA rotor magnet connected to the rotor, the VCA rotor magnet including a first VCA rotor magnet and a second VCA rotor magnet arranged in a bucking configuration, a third VCA rotor magnet positioned between the first VCA rotor magnet and the second VCA rotor magnet, the third VCA rotor magnet including a plurality of 90 degree segments magnetized in a radial orientation; and
      a VCA winding extending around the VCA rotor magnet.

15. The device of claim 14, further comprising:
   an actuator configured to selectively generate a rotating force to rotate the rotor relative to the stator.

16. The device of claim 14, further comprising:
   a motor controller configured to output control signals to the active longitudinal magnetic bearing to selectively position the rotor relative to the stator in the axial direction.

17. The device of claim 14, wherein the passive radial magnetic bearing includes a first passive magnetic bearing and a second passive magnetic bearing positioned at respective first and second ends of the rotor.

18. A device, comprising:
   a stator;
   a rotor configured to rotate relative to the stator;
   a passive radial magnetic bearing configured to support the rotor relative to the stator in a radial direction, the passive radial magnetic bearing comprising:
      a passive magnetic bearing (PMB) stator including a first PMB stator magnet and a second PMB stator magnet attached to the stator and arranged in a bucking configuration, with a non-magnet spacer situated between the first PMB stator magnet and the second PMB stator magnet; and a PMB rotor including a first PMB rotor magnet and a second PMB rotor magnet attached to the rotor and arranged in a bucking configuration;

an active longitudinal magnetic bearing configured to selectively position the rotor relative to the stator in an axial direction;

an actuator configured to selectively generate a rotating force to rotate the rotor relative to the stator, a position sensing magnet attached to the rotor;

a motor controller including a Hall Effect Sensor array configured to determine a position of the rotor relative to the stator based on the position sensing magnet;

a case having a first end and a second end, wherein the stator, the rotor, the passive radial magnetic bearing, the active longitudinal magnetic bearing, and the position sensing magnet are received in the case;

an impeller attached to the rotor at the first end of the case; and a circuit board having the Hall Effect Sensor array mounted thereon, the circuit board mounted at the second end of the case adjacent the sensing magnet.

19. The device of claim 18, wherein the Hall Effect Sensor array includes Hall Effect Sensors arranged in a circular array on the circuit board positioned circumferentially around a rotational axis of the rotor.

20. The device of claim 18, wherein the actuator is positioned between the position sensing magnet and the active longitudinal magnetic bearing in the axial direction.

* * * * *